(12) United States Patent
Johnson et al.

(10) Patent No.: US 10,679,754 B2
(45) Date of Patent: *Jun. 9, 2020

(54) SYSTEMS AND METHODS TO IMPROVE LUNG FUNCTION PROTOCOLS

(71) Applicant: General Electric Company, Schenectady, NY (US)

(72) Inventors: Christopher Donald Johnson, Niskayuna, NY (US); Peter Henry Tu, Niskayuna, NY (US); Andrew Phelps Day, Newtown, PA (US); Ting Yu, Niskayuna, NY (US); Jeffrey Richardson Terry, Dallas, TX (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,319

(22) Filed: Jul. 25, 2018

(65) Prior Publication Data

US 2018/0330827 A1 Nov. 15, 2018

Related U.S. Application Data

(63) Continuation of application No. 14/737,132, filed on Jun. 11, 2015, now Pat. No. 10,061,897.

(Continued)

(51) Int. Cl.
*G16H 20/40* (2018.01)
*G16H 50/30* (2018.01)
(Continued)

(52) U.S. Cl.
CPC ............. *G16H 50/30* (2018.01); *G06F 19/00* (2013.01); *G06F 19/3481* (2013.01); *G16H 20/40* (2018.01); *G16H 40/20* (2018.01)

(58) Field of Classification Search
CPC ...................................................... G16H 20/40
See application file for complete search history.

(56) References Cited

U.S. PATENT DOCUMENTS

2008/0106374 A1   5/2008   Sharbaugh
2008/0141301 A1   6/2008   Azzaro et al.
(Continued)

OTHER PUBLICATIONS

United States Patent and Trademark Office, "Notice of Allowance," issued in connection with U.S. Appl. No. 14/737,132, dated Apr. 27, 2018, 20 pages.

(Continued)

*Primary Examiner* — John A Pauls
(74) *Attorney, Agent, or Firm* — Hanley, Flight and Zimmerman, LLC

(57) ABSTRACT

An example method includes: classifying lung function risk based on patient attributes and a clinical protocol; generating alarms and incentives for compliance with the clinical protocol based on patient attributes, clinical protocol, and patient lung function risk; determining an orientation and position of a clinical device based on tagged feature(s) of the clinical device compared to identified patient feature(s); monitoring patient interaction with the clinical device; identifying a deviation from the clinical protocol based on the monitored patient interaction, a patient biometric indicator, and a desired setpoint state in the protocol; when a deviation is identified, providing feedback proportional to the deviation, the feedback including an adjustment with respect to the clinical protocol and/or the clinical device; and triggering at least one alarm and/or incentive based on deviation and feedback, wherein the alarm/incentives differs based on whether and to what extent deviation is identified and feedback.

18 Claims, 10 Drawing Sheets

Related U.S. Application Data

(60) Provisional application No. 62/010,842, filed on Jun. 11, 2014.

(51) Int. Cl.
    *G06F 19/00*     (2018.01)
    *G16H 40/20*     (2018.01)

(56) References Cited

U.S. PATENT DOCUMENTS

| | | |
|---|---|---|
| 2008/0146888 A1 | 6/2008 | Azzaro et al. |
| 2009/0089093 A1 | 4/2009 | Johnson et al. |
| 2009/0119126 A1 | 5/2009 | Johnson et al. |
| 2010/0305466 A1 | 12/2010 | Corn |
| 2012/0010901 A1 | 1/2012 | Johnson et al. |
| 2012/0066140 A1 | 3/2012 | Hegeman et al. |
| 2012/0154582 A1 | 6/2012 | Johnson et al. |
| 2015/0057485 A1 | 2/2015 | Carey et al. |
| 2015/0363566 A1 | 12/2015 | Johnson et al. |

OTHER PUBLICATIONS

United States Patent and Trademark Office, "Non-Final Office action," issued in connection with U.S. Appl. No. 14/737,132, dated Nov. 30, 2017, 35 pages.

SYSTEMS AND METHODS TO IMPROVE LUNG FUNCTION PROTOCOLS

CROSS-REFERENCE TO RELATED APPLICATIONS

This patent arises from a continuation of U.S. patent application Ser. No. 14/737,132, entitled "Systems and Methods To Improve Lung Function Protocols," filed on Jun. 11, 2015, which claims the benefit of U.S. patent application Ser. No. 62/010,842, entitled "Systems And Methods To Improve Lung Function Protocols Including Incentive Spirometry", filed Jun. 11, 2014, each of which is herein incorporated by reference in its entirety.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include, for example, patient medication orders, medical histories, imaging data, test results, diagnosis information, management information, and/or scheduling information, for example.

Protocol-centric environments are institutions such as hospitals, step down facilities, nursing and private homes, and the like. A hospital is used herein as an example of a protocol-centric environment. Adverse events that occur in hospitals, such as, for example, hospital-acquired pneumonia, result in patient harm, increased recovery time, unreimbursed healthcare costs, and loss of a hospital's and its staff's capacity to serve. One of the main causes of these events is non-adherence to protocols. As used herein, protocols refer to a series of preferred or prescribed tasks that (1) have been proven to reduce adverse events and (2) effect a desired elimination of activities, practices, or patterns that create harm or inefficiency. Example uses of such protocols are for hand washing, tube management (ventilator, urinary tract, and central line being examples), spirometry, and physical therapy. Protocols may be dually managed with a shared sensing and control system. For example, lung function protocols, having a shared attribute of being focused on breathing with aid of an apparatus interacting with the patient's nose, mouth, lungs and pulmonary biological/physical systems, can be managed together via a shared sensing and control system.

As an illustrative example, despite widespread knowledge that proper care plans, such as those for ventilators have associated protocols, which if followed, also reduce adverse events. Mortality rates for ventilator associated or acquired pneumonia that can be attributed to breaches in patient position and ventilator tube changing protocols range from approximately 25%-50% and can reach up to 76% in specific settings in the institutional care setting today, such as in hospitals. Estimates of the costs for one case of ventilator-associated pneumonia (VAP) have been reported to be $10,000-16,000 adding an estimated 4-32 additional ventilator days. Harm is therefore inflicted on the patient and a healthcare institution's ability to serve is diminished.

While there are many reasons for non-compliance (including a perceived lack of risk, time to wash, missing knowledge of protocol, or associated discomfort from complying with protocol and general inconvenience) improvement in protocols for hand sanitization before coming in contact with patients, mouth and skin care, tube exchange and lung exercise will reduce the spread of bacteria and thus lower the incidence of adverse events, thereby improving the standard of care. It is therefore advantageous to help the providers of healthcare and other persons involved in a patient's care or visitation to comply with protocols, including the patient themselves.

Many procedures benefit from a higher frequency of protocol compliance. Even relatively low level and treatable infections, such as a urinary tract infection, can escalate to life-threatening conditions including sepsis. Protocols to change tubes, if followed, will reduce the incidence of opportunities leading to infection onset. Protocols to ensure lung exercise will maximize the likelihood that air exchange capability is created.

Systems that have been developed to track and analyze activities in a clinical setting have focused primarily on single modality sensing, for example, Radio Frequency Identification (RFID) or infrared (IR) or manual key input or written bed board updates or human observatory monitoring schemas. As an example, one known RFID-based system focuses on identifying human activities in a hospital environment using Hidden Markov Models (HMMs) for supporting context-aware applications. While some manufacturing systems may incorporate a combination of RFID and computer vision, the multiple sensors are used to produce a discrete snapshot in time and do not provide contextual information over a period of time.

Typically, RFID and other protocol sensor systems take the form of location and contact make/break or pressure sensing for certain protocol adherence assuming that location association equates to protocol delivery or proper use of biomedical equipment by patients and care providers. This is a considerable failure point. As one example, an institution may specify that staff shall sanitize their hands upon entrance into the patient's room. Since there is little or no mechanism to reason what the staff is doing in the room or context, simple non-nuanced standing procedures are enforced. Sensor systems such as those that are IR or RFID-based determine if staff was in the presence of a hand sanitization station, or if cleansing agents are dispensed. A process defect is alarmed or recorded when staff enter a room and do not sanitize. In other systems, the provider of care wears a device to display they have hand sanitized but partially leave the protocol adherence determination to the patient for warning the care provider.

In non-healthcare domains, such as commercial shopping monitoring, humans in effect become the sensors with such programs as 'secret shoppers' and behavioral studies that use shopping patterns to infer consumer propensities to select product preferentially.

However, in such single modality systems a sensor must be associated with the patient, care provider, or apparatus being monitored, and infer that the proper contact has been made for a requisite time and orientation and clinical result. Further, such systems do not provide specific corrective control regarding specific behaviors, actions, and in-situ feedback. RFID systems are further limited by their range; typically RFID systems have a certain range of tolerance with respect to a tag (not hands or apparatus or contact) location.

In systems that employ optical sensing, optical tags may be used to identify objects such as specific equipment, patients, care providers, and sundry apparatus. Such systems typically provide optical or other tag information to a sensor and/or video record, may superimpose such information on a display, or may identify the orientation of a plurality of reference points for optical positioning for the purposes of diagnostic imaging or placement of apparatus such as biopsy needles but do not provide contextual guidance and incentives.

Therefore, it would be desirable to design a system and method for protocol adherence which precisely tracks, over time, hand surface, apparatus position, and dynamical action context with respect to tasks prescribed in the protocol, so that care protocols may be intervened into in real time and may be used for engaging the patient and be used for staff skill building—ultimately enabling superior medical outcomes in delivery of care by personnel who are tasked with ever more acute cases and census. Further that the control system would provide incentives for patients through time to stay on protocol for those who can self administer while for those patients who are impaired, the system would tightly control the delivery of care by other persons or mechanical systems. Such tracking, engagement, control, intervention, and improvement cannot be found in the prior art.

BRIEF SUMMARY

Certain examples provide systems and methods to monitor and incentivize execution of a lung function-related clinical protocol.

An example method includes: classifying lung function risk, based on patient attributes and a clinical protocol; generating alarms and incentives for compliance with the clinical protocol based on patient attributes, clinical protocol, and patient lung function risk; determining an orientation and position of a clinical device based on tagged feature(s) of the clinical device compared to identified patient feature(s); monitoring patient interaction with the clinical device; identifying a deviation from the clinical protocol based on the monitored patient interaction, a patient biometric indicator, and a desired setpoint state in the protocol; when a deviation is identified, providing feedback proportional to the deviation, the feedback including an adjustment with respect to the clinical protocol and/or the clinical device; and triggering at least one alarm and/or incentive based on deviation and feedback, wherein the alarm/incentives differs based on whether and to what extent deviation is identified and feedback.

Example computer-readable media, systems, and/or other apparatus can be used to implement methods disclosed herein.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

Figure 1:
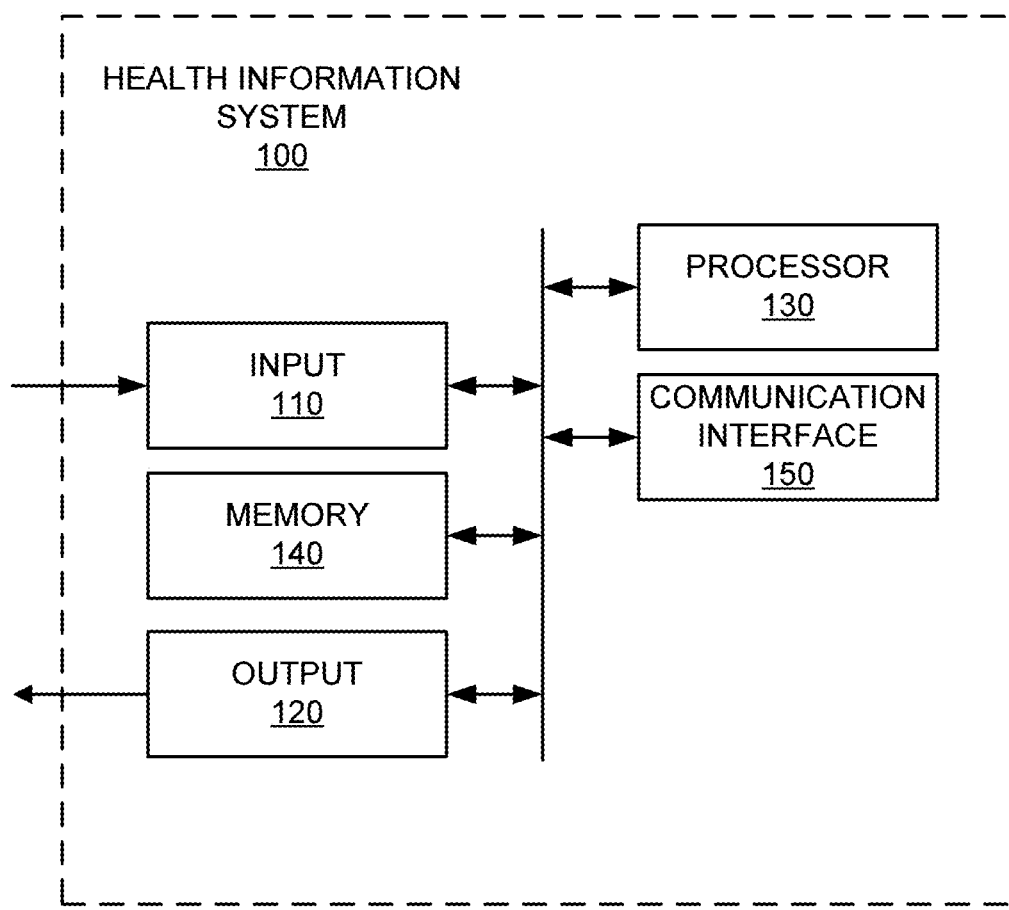
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Certain examples provide systems and methods to monitor and incentivize execution of a lung function-related clinical protocol using a clinical device. For example, certain examples provide systems and methods to help control the delivery of lung function related protocols for patients who are able to care for themselves (spirometry) and those whose lung function is severely impaired (ventilator). Certain examples facilitate incentive spirometry and compliance with associated lung function protocols for self-administration. Certain examples provide closed loop control for ventilator administration, ensuring that oral care, lung exercises and tubes are explicitly managed to the standard of care. Certain examples help improve participation rate and quality of incentivized protocol adherence, such as spirometry, with closed-loop monitoring, automated set point selection, feedback, and social reinforcement control. Spirometry is used as an example of activating social networks into delivery of medical protocols for incentive building and for activating analytical communities with high dimensional, high precision training data for decision support and reasoning algorithms that can be consumed by and used for protocol delivery, monitoring, feedback and control. Ventilator is used as an example of activating closed loop control of care protocols related to the interaction of biomedical devices with the mouth and lungs of patients. Other examples are envisioned and enabled by the following description and disclosure.

Certain examples of the presently disclosed technology improve a participation rate and quality of self-incentivized protocol adherence, such as spirometry, ventilator protocol(s), oxygen mask usage, etc., with closed-loop monitoring systems and methods, set point selection, feedback, and social reinforcement.

Certain medical protocols are specified in a patient's care plan to help them heal and/or lower risk of developing an adverse condition. These protocols are successful if appropriately chosen for a patient's specific condition and if the patient and/or care provider(s) actually performs the prescribed actions.

In many cases, these protocols, when being performed, create discomfort and therefore a disincentive to perform the protocol. A human tendency to minimize the actions creating discomfort can be offset by providing goals and indicators toward a desired measure. For example, as a patient experiences physical discomfort in complying with a protocol element, a feedback signal is also being generated from the activity and is used to create an incentive for the patient to reach a goal associated with the protocol, protocol element, measure, etc.

In certain examples, goals are static in nature, and are updated periodically as a patient's progress is considered through manual or automated analysis. For example, it can be difficult for a care provider to ad-hoc or episodically determine an actual rate of progress, and there is no practical way to record and then analyze the performance of the prescribed activity or the quality or measure of the activity to gauge progress towards a goal. Dynamic goals that pace just far enough ahead of a patient's current ability in order to accelerate capability development or restoration are often not possible due to lack of measures in dimensions of both activity and quality.

Many aspects of care compliance can be self-regulated rather than paying for human (non-patient) manual efforts, monitoring and recording of data or even coaching or motivation. Typically, humans respond to encouragement to augment their own internal motivations. In considering a protocol, performance of which creates discomfort, whose activity occurs predominantly in isolation, whose schedule is easily forgotten and whose rate of progress may not actually be known nor goals updated infrequently, medical outcomes that otherwise could have been realized are unrealized in current approaches.

Clinical decision support reasoning algorithms can be forward or reverse chaining if-then-else triggers regarding a person's compliance to or progress from a protocol. This limitation occurs due to episodic charting and low gauge repeatability and reliability of the recorded measures. In other domains, where data quality allows and new features are added to the data, classes of algorithms from the machine learning art, for example, are able to train over enhanced feature space to characterize the state of systems with a high degree of precision. A diversity of algorithms, each constructed with different feature selection and method, describe the observed in a diverse way. A multitude of these diverse models can increase the specificity of a detection by creating ever more nuanced and specific activity detection as well as acting as a confidence enhancement for the automated detection of the same activity with multiple reasoning engines whose outputs are fused.

For example, consider enhancing lung function in hospitalized patients, many of whom have had surgery in the chest cavity with general anesthesia and are oriented in a bed. These patients are at risk of fluid build-up and decreased lung function as the alveoli sacks are not opened up without backpressure. An incentive spirometry protocol can be prescribed so as to create opportunities for that requisite back pressure. In spirometry, the patient is given volume and rate feedback from a mechanical device. Care providers compare the observed volume and rate to the prescribed goal and chart the status. The patient is instructed to use the spirometer for, as an example, ten (10) breaths every hour, in breathing in slowly at a goal rate to achieve a goal volume of air and to exhale at a goal rate to achieve a backpressure. The nurse may make rounds every several hours, and thus it is up to the patient to execute this protocol.

In certain examples, close loop controlled ventilator use, such as is disclosed herein, reduce or minimize ventilator acquired pneumonia (VAP) by having a patient, for short and specific durations, breath using their own lung muscles, have their teeth and mouth cleaned once or twice daily with a specified contact duration, have ventilator tubes exchanged over a specified cycle of days and have the patient's torso elevated during a specified period of time throughout the day.

Certain examples overcome these limitations with protocol selection, a standoff optical measuring system, a reasoning system, automated data source for charting, dynamic feedback for the patient to both remind them to use the device and their progress, and to engage social incentives from patient stakeholders who could be cohorts also in a given hospital or a network of hospitals or a social network. Enabling the fullest social participation while also maintaining anonymity and discretion is overcome with a rendering capability which captures the form of a person's activity and projects it, if chosen to, in outline, avatar, or comic format. An alert replaces a lack of human witness of protocol execution. These alerts are for compliance with a protocol and focus staff interventions for targeted patient coaching. Additionally, certain examples facilitate development of detection algorithms by others.

The systems and methods disclosed and described herein provide an integrated and automated workflow, sensor, and reasoning system that automatically detect breaches in protocols, appropriately alarms and record these breaches, facilitate staff adoption of protocol adherence, and ultimately enable the study of protocols for care comparative effectiveness. An example system provides real-time alerts to medical personnel in the actual processes of care, thereby reducing the number of negative patient events and ultimately improving staff behavior with respect to protocol adherence.

An optically based sensor system is deployed that determines the location and trajectory of people as well as the presence of certain objects and settings or status of configured apparatus, which singularly or in conjunction with other analog and digital data, informs a reasoning engine that calculates the state of the monitored people and objects. Deviations from desired states are determined and appropriate reporting and alarming is made. The sensor and reasoning systems are hosted in a message brokered computing environment that may persist in one or more computers and locations.

Certain examples address a considerable failure point in tradition RFID sensor systems which provide only simple non-nuanced procedures that merely determine whether staff is in a room, rather than what the staff is doing in that room.

Location assessment alone may not equate to protocol delivery or proper use of biomedical equipment by patients and care providers.

As opposed to single modality systems that associate a particular sensor with a patient, care provider, or apparatus being monitored, certain examples provide information regarding specific behaviors, actions, and in-situ feedback. Certain examples determine whether specific behaviors and actions are occurring according to specified temporal-spatial relationships such as teeth being brushed, lips moisturized, masks seated, tubes set or exchanged properly, a patient's orientation is as specified, etc., through time. Certain examples provide in-situ feedback, contextually appropriate workflow and/or insightful summary reporting so that care providers are specifically informed at which point protocols broke down, for patients to properly control their own care or be incentivized to maintain a regime, especially when required to overcome discomfort.

A goal of the disclosed system is to modify the behavior of medical staff and visitors with respect to patient care quality. Humans cannot multitask beyond a certain point and maintain the quality of individual tasks as though those tasks were being singularly focused upon. As such, reminders as to proper protocols can prevent situations that will ultimately lead to quality of care degradation. To this end, the system can continually monitor patient room activity to detect and/or predict breaches with respect to a specified set of protocols with great precision as fine as apparatus-to-skin contact in the correct anatomical orientation and constancy. As used herein, "protocols" refer to an ordered sequence of events or tasks or motions, events or tasks with deterministic or conditional path dependence or checklists that may or may not have an ordered temporal or spatial preference. In the healthcare example, protocols include policy, tasks, clinical events, regulatory events, administrative events specified for the care of patients. Such protocols may, as examples, include hand washing before and after interacting with a patient, monitoring rounds of care givers, monitoring physical activity of patients, monitoring patient positions and making sure that patients, especially sedentary ones, are turned on a regular basis so as to prevent the occurrence of pressure ulcers, cleaning protocols, therapeutic protocols such as spirometry or muscular-skeletal stretches or activity and scheduling protocols. Certain examples can be used in training, in-situ monitoring, to record events and state changes in other systems such as medical event reporting or bed boards or the system's own activity record.

Examples set forth herein focus on the monitoring of tasks, which are specified a-priory, that comprise a protocol using information from databases, sensor systems, motion and optical shape recognition in the healthcare clinical services delivery venue. This system captures inputs or state changes from the art of computer vision object, movement and persons identification, telemetry, signal processing, sensor systems and electronic records in order to uniquely reason or identify the state of activities being monitored relative to prescribed protocols. An ability to uniquely identify an entity is achieved by temporal and spatial patterns, observed people and device geometries, either or both of targets or shapes and in conjunction with optical beaconing or radio frequency identification. An ability to transform state space information into decision support that can be acted upon is derived from the disclosed system's workflow logic. Workflow configuration, interdependencies and specification, sensing, reasoning of state space and alerting or reporting are implemented on computer systems using computer code on single or networked devices.

While the detailed description focuses on "medical staff," "care provider," and "stakeholder," a skilled artisan will recognize that the system and method may be applied to any person interacting with the patient, including visitors as an example. Further, while the system and method set forth herein is described with respect to a healthcare clinical process, it can be readily appreciated that the system and method is equally applicable to other human process activities that involve humans and protocols to achieve objectives, such as, for example, manufacturing, food preparation, apparatus service, training, customer service, security, etc.

Certain examples depart from the current methods and systems in a number of ways. For example, embodiments include a real time system comprising software and hardware modules that are integrated into real-time hospital operational workflow and work together to understand activities in a monitored environment, determine whether the activities conform to explicit or implicit protocols, and to automatically tailor communication (e.g., message, channel, and intensity) to change behavior that results in adverse events. In "closing the protocol loop," the tasks can be accurately monitored and feedback provided both directly on the prescribed protocol as well as for pattern discovery. Accordingly, embodiments may be used to improve the patient flow, maximize staff utilization, minimize unnecessary length of stay, and ultimately, improve the financial sustainability of the overall hospital system. Success for the system implies an improvement of medical staff and visitor behavior with regard to such protocols after a certain period of use, thus resulting in fewer adverse medical events and/or negative patient outcomes (e.g., infection, falls and pressure ulcers).

Examples include a number of key continuous functions, including care plans that invoke protocols and sub tasks that must be executed and transform the protocols into time, space, and resource ordered tasks that are queued for monitoring. Also, a combination of multi-modal sensors and computer vision is used to identify motion, objects, and people alone or in combination with data and traditional sensor inputs and analyze activity analysis (e.g., through reasoning over 1 or more sensor signals). A reasoning engine is then used to determine the state of the systems and tasks related to the protocols. Such combination may include the use of telemetry, computer vision, radio frequency identification (RFID), audio analysis, commercial sensor technology, and the like.

A reasoning engine may be used, for example, for anomaly detection (e.g., "agent A is violating protocol task X"). In addition, embodiments dynamically direct workflow in such a way as to minimize adverse events and overall process flow constraints. Accordingly, embodiments of the disclosed system may be used to minimize adverse events in protocol-centric environments, such as breaches in patient care protocols, infections, falls, and other hospital-acquired conditions, thereby reducing patient harm.

Further, embodiments disclosed herein form a system of systems that enable discrete and corporate response via the use of message brokering to facilitate a multitude of sensors, algorithms, and computing infrastructure.

Accompanying this technology is a comprehensive human motivational method that facilitates the building of a shared vision for dramatically reducing the lapses in protocol adherence that contributes to adverse events. This is facilitated by the impartial, continuous fact-based feedback which the disclosed provides. For example, embodiments present fact-based feedback to humans for contextual feedback for the purposes of incentivized compliance or goal seeking in the case of a patient or professional development and behavioral change influencing (e.g., real-time audible notification, post-event aggregation, analysis, and reporting, etc.) in the case of a provider of care. Where clinical care adverse medical event reduction, behavioral change, and skill building is a focus, a means to monitor the delivery of proper protocol steps and provide real time guidance relative to the desired protocol will improve the consistency of medical care and improve medical staff behavior with respect to protocol adherence.

Accordingly, systems and methods disclosed herein manage a clinical workflow to deliver appropriate protocols, unobtrusively monitor associated steps, determine if the care is being delivered within the specified clinical practice guidelines, and alert providers to lapses of procedure, for example.

II. Example Operating Environment

Health information, also referred to as healthcare information and/or healthcare data, relates to information generated and/or used by a healthcare entity. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. Example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

A. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100.

Example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of example system 100 can be integrated in one device or distributed over two or more devices.

Example input 110 may include a keyboard, a touch-screen, a mouse, a trackball, a track pad, optical barcode recognition, voice command, etc. or combination thereof used to communicate an instruction or data to system 100. Example input 110 may include an interface between systems, between user(s) and system 100, etc.

Example output 120 can provide a display generated by processor 130 for visual illustration on a monitor or the like. The display can be in the form of a network interface or graphic user interface (GUI) to exchange data, instructions, or illustrations on a computing device via communication interface 150, for example. Example output 120 may include a monitor (e.g., liquid crystal display (LCD), plasma display, cathode ray tube (CRT), etc.), light emitting diodes (LEDs), a touch-screen, a printer, a speaker, or other conventional display device or combination thereof.

Example processor 130 includes hardware and/or software configuring the hardware to execute one or more tasks and/or implement a particular system configuration. Example processor 130 processes data received at input 110 and generates a result that can be provided to one or more of output 120, memory 140, and communication interface 150. For example, example processor 130 can take user annotation provided via input 110 with respect to an image displayed via output 120 and can generate a report associated with the image based on the annotation. As another example, processor 130 can process updated patient information obtained via input 110 to provide an updated patient record to an EMR via communication interface 150.

Example memory 140 may include a relational database, an object-oriented database, a data dictionary, a clinical data repository, a data warehouse, a data mart, a vendor neutral archive, an enterprise archive, etc. Example memory 140 stores images, patient data, best practices, clinical knowledge, analytics, reports, etc. Example memory 140 can store data and/or instructions for access by the processor 130. In certain examples, memory 140 can be accessible by an external system via the communication interface 150.

In certain examples, memory 140 stores and controls access to encrypted information, such as patient records, encrypted update-transactions for patient medical records, including usage history, etc. In an example, medical records can be stored without using logic structures specific to medical records. In such a manner, memory 140 is not searchable. For example, a patient's data can be encrypted with a unique patient-owned key at the source of the data. The data is then uploaded to memory 140. Memory 140 does not process or store unencrypted data thus minimizing privacy concerns. The patient's data can be downloaded and decrypted locally with the encryption key.

For example, memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories. Document information may include an identifier, a patient identifier, a clinic identifier, a security category, and encrypted data, for example.

Example communication interface 150 facilitates transmission of electronic data within and/or among one or more systems. Communication via communication interface 150 can be implemented using one or more protocols. In some examples, communication via communication interface 150 occurs according to one or more standards (e.g., Digital Imaging and Communications in Medicine (DICOM), Health Level Seven (HL7), ANSI X12N, etc.). Example communication interface 150 can be a wired interface (e.g., a data bus, a Universal Serial Bus (USB) connection, etc.) and/or a wireless interface (e.g., radio frequency, infrared, near field communication (NFC), etc.). For example, communication interface 150 may communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

B. Example Healthcare Infrastructure

Figure 2:
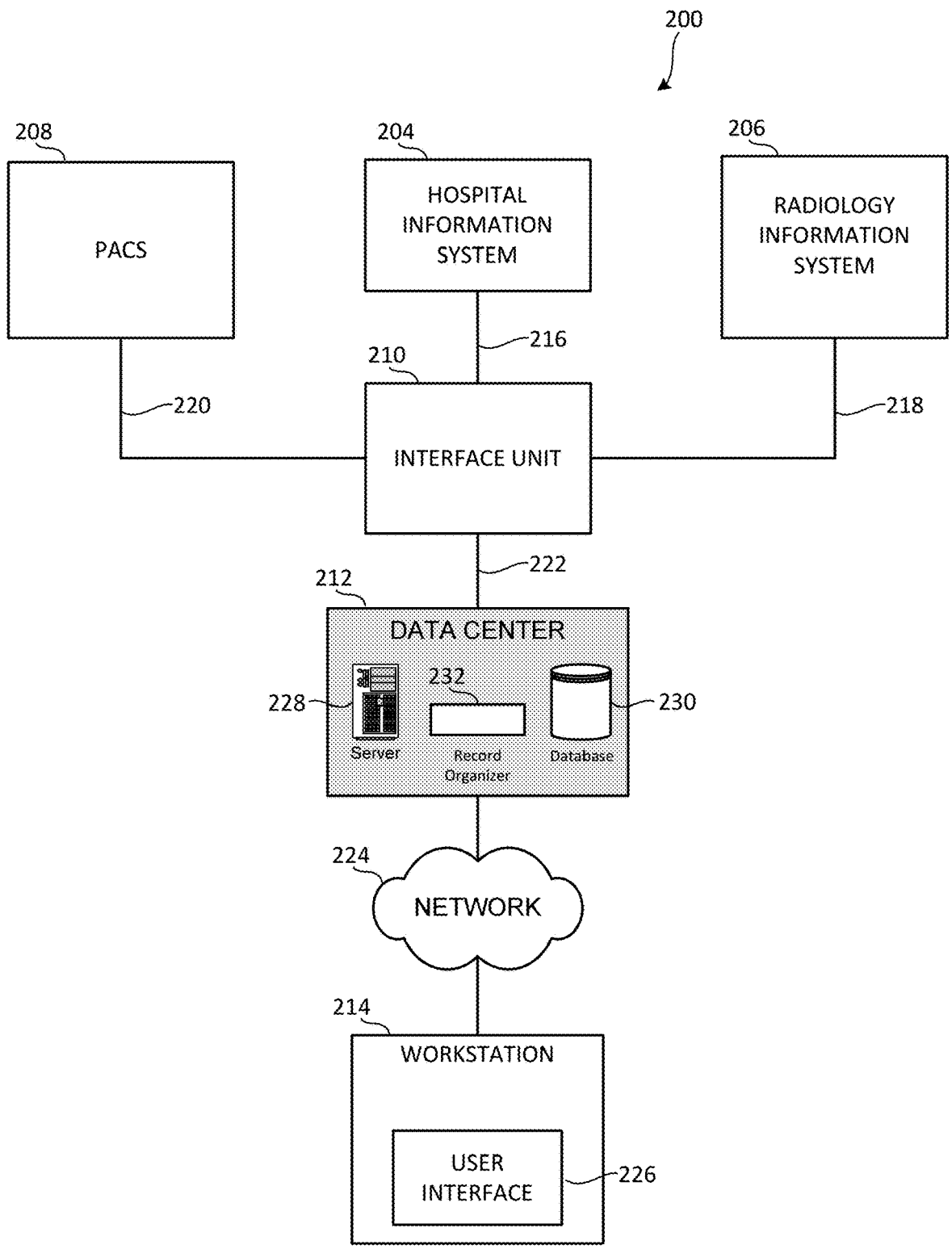
FIG. 2 shows a block diagram of an example healthcare information infrastructure including one or more systems.

FIG. 2 shows a block diagram of an example healthcare information infrastructure 200 including one or more sub-systems such as the example healthcare-related information system 100 illustrated in FIG. 1. Example healthcare system 200 includes a HIS 204, a RIS 206, a PACS 208, an interface unit 210, a data center 212, and a workstation 214. In the illustrated example, HIS 204, MS 206, and PACS 208 are housed in a healthcare facility and locally archived. However, in other implementations, HIS 204, MS 206, and/or PACS 208 may be housed within one or more other suitable locations. In certain implementations, one or more of PACS 208, MS 206, HIS 204, etc., may be implemented remotely via a thin client and/or downloadable software solution. Furthermore, one or more components of the healthcare system 200 can be combined and/or implemented together. For example, MS 206 and/or PACS 208 can be integrated with HIS 204; PACS 208 can be integrated with RIS 206; and/or the three example information systems 204, 206, and/or 208 can be integrated together. In other example implementations, healthcare system 200 includes a subset of the illustrated information systems 204, 206, and/or 208. For example, healthcare system 200 may include only one or two of HIS 204, MS 206, and/or PACS 208. Information (e.g., scheduling, test results, exam image data, observations, diagnosis, etc.) can be entered into HIS 204, MS 206, and/or PACS 208 by healthcare practitioners (e.g., radiologists, physicians, and/or technicians) and/or administrators before and/or after patient examination. One or more of the HIS 204, MS 206, and/or PACS 208 can communicate with equipment and system(s) in an operating room, patient room, etc., to track activity, correlate information, generate reports and/or next actions, and the like.

The HIS 204 stores medical information such as clinical reports, patient information, and/or administrative information received from, for example, personnel at a hospital, clinic, and/or a physician's office (e.g., an EMR, EHR, PHR, etc.). MS 206 stores information such as, for example, radiology reports, radiology exam image data, messages, warnings, alerts, patient scheduling information, patient demographic data, patient tracking information, and/or physician and patient status monitors. Additionally, MS 206 enables exam order entry (e.g., ordering an x-ray of a patient) and image and film tracking (e.g., tracking identities of one or more people that have checked out a film). In some examples, information in MS 206 is formatted according to the HL-7 (Health Level Seven) clinical communication protocol. In certain examples, a medical exam distributor is located in MS 206 to facilitate distribution of radiology exams to a radiologist workload for review and management of the exam distribution by, for example, an administrator.

PACS 208 stores medical images (e.g., x-rays, scans, three-dimensional renderings, etc.) as, for example, digital images in a database or registry. In some examples, the medical images are stored in PACS 208 using the Digital Imaging and Communications in Medicine (DICOM) format. Images are stored in PACS 208 by healthcare practitioners (e.g., imaging technicians, physicians, radiologists) after a medical imaging of a patient and/or are automatically transmitted from medical imaging devices to PACS 208 for storage. In some examples, PACS 208 can also include a display device and/or viewing workstation to enable a healthcare practitioner or provider to communicate with PACS 208.

The interface unit 210 includes a hospital information system interface connection 216, a radiology information system interface connection 218, a PACS interface connection 220, and a data center interface connection 222. Interface unit 210 facilities communication among HIS 204, RIS 206, PACS 208, and/or data center 212. Interface connections 216, 218, 220, and 222 can be implemented by, for example, a Wide Area Network (WAN) such as a private network or the Internet. Accordingly, interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with workstation 214, via a network 224, implemented at a plurality of locations (e.g., a hospital, clinic, doctor's office, other medical office, or terminal, etc.). Network 224 is implemented by, for example, the Internet, an intranet, a private network, a wired or wireless Local Area Network, and/or a wired or wireless Wide Area Network. In some examples, interface unit 210 also includes a broker (e.g., a Mitra Imaging's PACS Broker) to allow medical information and medical images to be transmitted together and stored together.

Interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), interface unit 210 translates or reformats (e.g., into Structured Query Language ("SQL") or standard text) the medical information, such as medical reports, to be properly stored at data center 212. The reformatted medical information can be transmitted using a transmission protocol to enable different medical information to share common identification elements, such as a patient name or social security number. Next, interface unit 210 transmits the medical information to data center 212 via data center interface connection 222. Finally, medical information is stored in data center 212 in, for example, the DICOM format, which enables medical images and corresponding medical information to be transmitted and stored together.

The medical information is later viewable and easily retrievable at workstation 214 (e.g., by their common identification element, such as a patient name or record number). Workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. Workstation 214 receives commands and/or other input from a user via, for example, a keyboard, mouse, track ball, microphone, etc. Workstation 214 is capable of implementing a user interface 226 to enable a healthcare practitioner and/or administrator to interact with healthcare system 200. For example, in response to a request from a physician, user interface 226 presents a patient medical history. In other examples, a radiologist is able to retrieve and manage a workload of exams distributed for review to the radiologist via user interface 226. In further examples, an administrator reviews radiologist workloads, exam allocation, and/or operational statistics associated with the distribution of exams via user interface 226. In some examples, the administrator adjusts one or more settings or outcomes via user interface 226.

Example data center 212 of FIG. 2 is an archive to store information such as images, data, medical reports, and/or, more generally, patient medical records. In addition, data center 212 can also serve as a central conduit to information located at other sources such as, for example, local archives, hospital information systems/radiology information systems (e.g., HIS 204 and/or RIS 206), or medical imaging/storage systems (e.g., PACS 208 and/or connected imaging modalities). That is, the data center 212 can store links or indicators (e.g., identification numbers, patient names, or record numbers) to information. In the illustrated example, data center 212 is managed by an application server provider (ASP) and is located in a centralized location that can be accessed by a plurality of systems and facilities (e.g., hospitals, clinics, doctor's offices, other medical offices, and/or terminals). In some examples, data center 212 can be spatially distant from HIS 204, MS 206, and/or PACS 208.

Example data center 212 of FIG. 2 includes a server 228, a database 230, and a record organizer 232. Server 228 receives, processes, and conveys information to and from the components of healthcare system 200. Database 230 stores the medical information described herein and provides access thereto. Example record organizer 232 of FIG. 2 manages patient medical histories, for example. Record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by system 200 via a software-as-a-service (SaaS) implementation over a cloud or other computer network, for example. In certain examples, all or part of system 200 can also be provided via platform as a service (PaaS), infrastructure as a service (IaaS), etc. For example, system 200 can be implemented as a cloud-delivered Mobile Computing Integration Platform as a Service. A set of consumer-facing Web-based, mobile, and/or other applications enable users to interact with the PaaS, for example.

C. Industrial Internet Examples

The Internet of things (also referred to as the "Industrial Internet") relates to an interconnection between a device that can use an Internet connection to talk with other devices on the network. Using the connection, devices can communicate to trigger events/actions (e.g., changing temperature, turning on/off, providing a status, etc.). In certain examples, machines can be merged with "big data" to improve efficiency and operations, provide improved data mining, facilitate better operation, etc.

Big data can refer to a collection of data so large and complex that it becomes difficult to process using traditional data processing tools/methods. Challenges associated with a large data set include data capture, sorting, storage, search, transfer, analysis, and visualization. A trend toward larger data sets is due at least in part to additional information derivable from analysis of a single large set of data, rather than analysis of a plurality of separate, smaller data sets. By analyzing a single large data set, correlations can be found in the data, and data quality can be evaluated.

Figure 3:
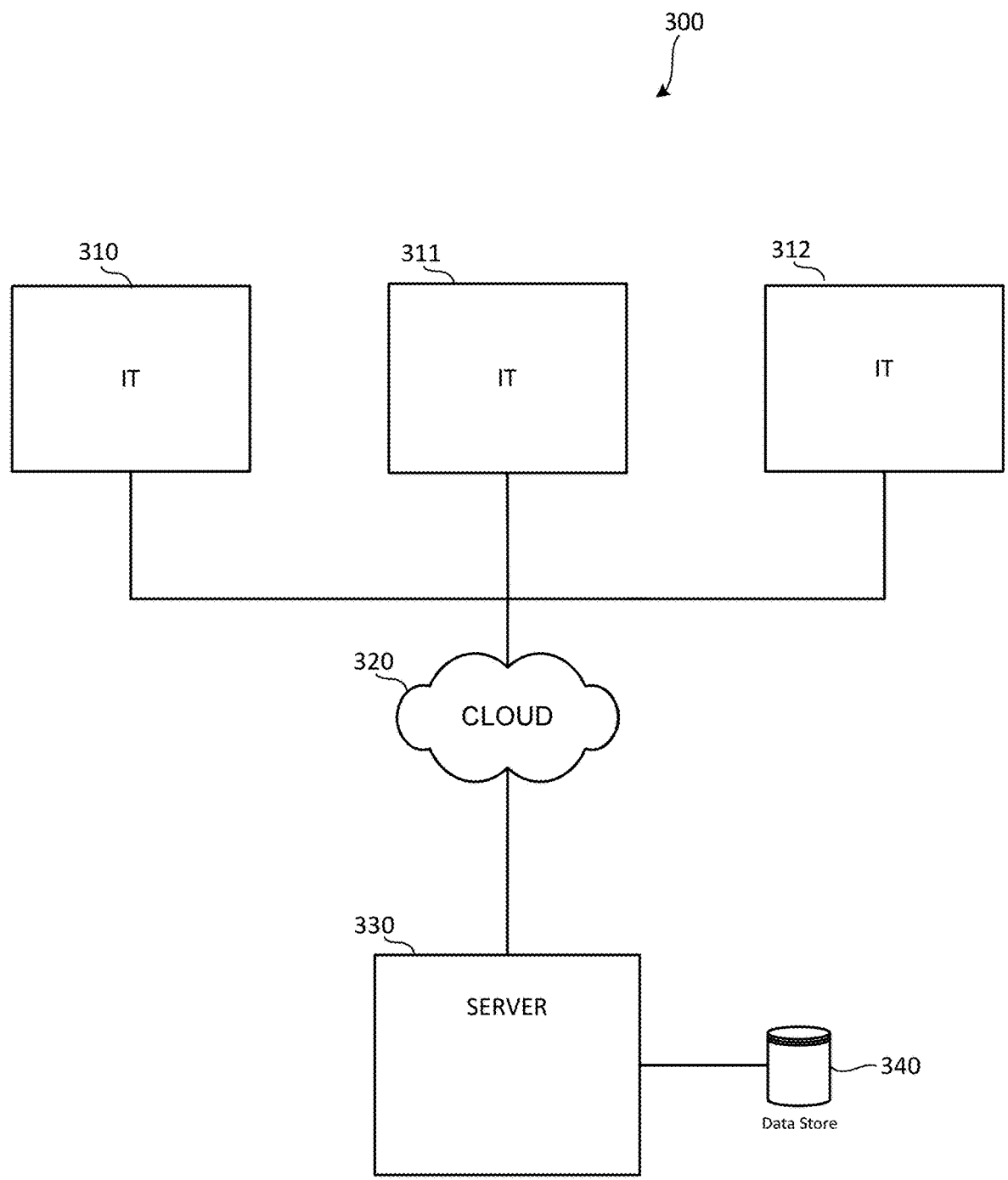
FIG. 3 shows an example industrial internet configuration including a plurality of health-focused systems.

FIG. 3 illustrates an example industrial internet configuration 300. Example configuration 300 includes a plurality of health-focused systems 310-312, such as a plurality of health information systems 100 (e.g., PACS, RIS, EMR, etc.) communicating via industrial internet infrastructure 300. Example industrial internet 300 includes a plurality of health-related information systems 310-312 communicating via a cloud 320 with a server 330 and associated data store 340.

As shown in the example of FIG. 3, a plurality of devices (e.g., information systems, imaging modalities, etc.) 310-312 can access a cloud 320, which connects the devices 310-312 with a server 330 and associated data store 340. Information systems, for example, include communication interfaces to exchange information with server 330 and data store 340 via the cloud 320. Other devices, such as medical imaging scanners, patient monitors, etc., can be outfitted with sensors and communication interfaces to enable them to communicate with each other and with the server 330 via the cloud 320.

Thus, machines 310-312 within system 300 become "intelligent" as a network with advanced sensors, controls, analytical based decision support and hosting software applications. Using such an infrastructure, advanced analytics can be provided to associated data. The analytics combines physics-based analytics, predictive algorithms, automation, and deep domain expertise. Via cloud 320, devices 310-312 and associated people can be connected to support more intelligent design, operations, maintenance, and higher server quality and safety, for example.

Using the industrial internet infrastructure, for example, a proprietary machine data stream can be extracted from a device 310. Machine-based algorithms and data analysis are applied to the extracted data. Data visualization can be remote, centralized, etc. Data is then shared with authorized users, and any gathered and/or gleaned intelligence is fed back into the machines 310-312.

D. Data Mining Examples

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

E. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

III. Example Lung Function Improvement and Monitoring Systems

While improved lung function may be desired for patients after surgery and a general prescription may be made, specific targets of lung volume, flow rate, spirometry patterns, and patient incentives have an opportunity for specific customization and goal setting.

Spirometry relates to measuring of breath and is a pulmonary function test (PFT) to measure lung function, particularly an amount (volume) and/or speed (flow velocity) of air that can be inhaled and exhaled. Spirometry can be used to generate pneumotachographs, which can be used to assess conditions such as asthma, pulmonary fibrosis, cystic fibrosis, and COPD.

By way of example, an eighty-five (85) year old male returning from surgery under general anesthesia for an operation of the pancreas may have a more beneficial goal set for volume, rate and frequency than a similar 85 year old male - with the same operation but also a co-morbidity of congestive heart failure onset. Further, a desired lung function rate of change goal may be different as well as the adaptation of the protocol to positive or negative response to the therapy. Further still, these two patients may diverge with respect to the degree or form of incentive that will help them stay in compliance with the protocol.

Figure 4:
FIG. 4 illustrates a flow diagram for a method to establish spirometry goals and incentives

Referring to FIG. 4, a flow diagram shows an example method 400 to obtain and utilize a sequence of information to guide the selection and setting of spirometry goals and incentives 400. Spirometry use by a patient may be associated with a treatment protocol for that patient, for example. In certain examples, at block 405, patient attribute data, such as a patient's age, medical history, weight, health state, biometrics, medications, sedation type and duration, and/or other factors can be used by regression and machine learning algorithms to more precisely match beneficial protocol settings to a given patient.

Spirometry is one component of a clinical pathway that includes diagnostics, surgical services, therapy, medication delivery, etc. People, objects, motion, and visual signals such as displays, coupled with other data from various systems are acquired to determine a state of the environment (the system and its stakeholders) relative to the tasks of the protocol, for example. At block 410, elements and type of care pathway or care plan are determined as an input so that the specific settings of the spirometry protocol may be further specified.

Certain care plans are determined as appropriate and desirable for the patient. The first continuous function is illustrated upon admittance to the institution or as prescribed by a healthcare professional when extending the monitoring of protocols to other venues such as the home. Within care plans, there are typically protocols of care that have been found to be advantageous for treating medical conditions or accomplishing clinical tasks. These protocols are established by, for example, medical societies, hospitals and healthcare providers. Some protocols are "standing" and stay in effect for the duration of care while others are specific to a circumstance. These protocols can be singularly developed or via collaborations and may be purchased or licensed with alone or accompanied by markers or other devices as part of a packaged solution.

In addition to the patient features 405 and the scheduled clinical activity 410, at block 415, a patient's lung function risk is ascertained from the medical professional or received automatically from the system as a result of the patient attributes 405 and procedure type 410. In either embodiment, a risk of degraded lung function is estimated and a classification 415 is made that can be used to select protocol features and intensity and alarm set points for non-compliance. The classification 415 is tied to a capability of an institution to deliver protocols, for example (e.g., not every bed may have the disclosed measuring system, and, therefore, only those patients at the highest risk may be assigned the beds with the system).

At block 420, given the patient data 405, procedure(s) causing the patient to be at the hospital 410, lung function risk of the patient 415, available resources to deliver a given protocol such as a monitored bed being available, etc., a best lung function protocol is selected for that patient, informed by the responses to past protocol deliveries for other patients.

At block 425, similar patients, past or current, who understand the benefits of spirometry or are similarly in need of complying with a regime of spirometry form a candidate pool for selecting an incentive cohort. There may be multiple cohort groups such as family or other stakeholders of the patient or other interested parties. The cohort group(s) provide a positive social reinforcing loop from motivations provided to the patient from others 'in the same boat', friends, family or others who are interested for their own reasons and are now beneficially connected to the patient. The cohort is selected by knowledge or interest of the patient, such as for family. The cohort may be assigned with a rule such as a standing order in the protocol to have all patients using spirometry be networked or all patients with cardiac procedures or all females below forty (40), etc. Further, the cohort may be selected beyond a given hospital and networked with many participating institutions. As the pool of candidates for the incentive cohort expands, the selection of individual members is informed by the incentive response likelihood as determined from the responses of past patients (with similar features as the current patient) to other persons.

At block 430, a frequency pattern of spirometry is established for the patient. The frequency pattern can be based upon the responses and outcomes of prior patients of similar attribute 405, 410, 415, 420. One patient may have a goal established of fifteen (15) breaths per hour. Another patient, as a result of this decision step or clinical judgment may be given a ten (10) breath target of any rate or volume, every two (2) hours. Another patient may be specified to have as a goal to use the spirometer every hour, for example.

At block 435, an intensity of spirometry is established for the patient. The intensity can be based upon the responses and outcomes of prior patients of similar attribute 405, 410, 415, 420, and factoring in the frequency 430. One patient may have a goal established of fifteen (15) breaths of a certain milliliter (mL) volume and/or mL/minute (min) rate per hour of the day, further specified as a different volume or flow rate for each hour or other time division of the day. Intensity set point goals may be raised over a course of treatment, such as to follow an expected improvement. Another patient, as a result of this decision step or clinical judgment may be given a ten (10) breath target of any rate or volume, every two (2) hours. Another patient may be specified to have as a goal to use the spirometer every hour, irrespective of the rate or volume of air breathed.

At block 440, feedback loop and alarm settings are established using the protocol 420 and selected target set points for frequency 430 and intensity 435. Any combination of protocol miss may be specified as alarmable, and there may be any number of different alarms established and sent to any number of specified people or roles, for example.

At block 445, spirometry incentives and alarm designations are sent to related entities. In one example, an alarm is sent to a charge nurse if a patient has not used the spirometer in the last twelve (12) hours. In another example, an alarm is sent to an EMR for triggering a clinical review by a surgeon if the patient has not established 1000 mL of breath in a 42 second interval by 1600 hours on the day after surgery. In another example, an alert is sent to an incentive cohort when the protocol has been missed for two consecutive periods. The combinations of metrics to trigger an alarm 440 and alarm destination 445 is expansive. In certain examples, these may be set by selection or an algorithm which beneficially uses a training set from prior patients and the current patient's feature set, actions and responses. The alarms may be considered adverse or positive. A positive example includes a score that is published or points that are earned. These trigger points 440, 445 are established for management by the system.

Figure 5:
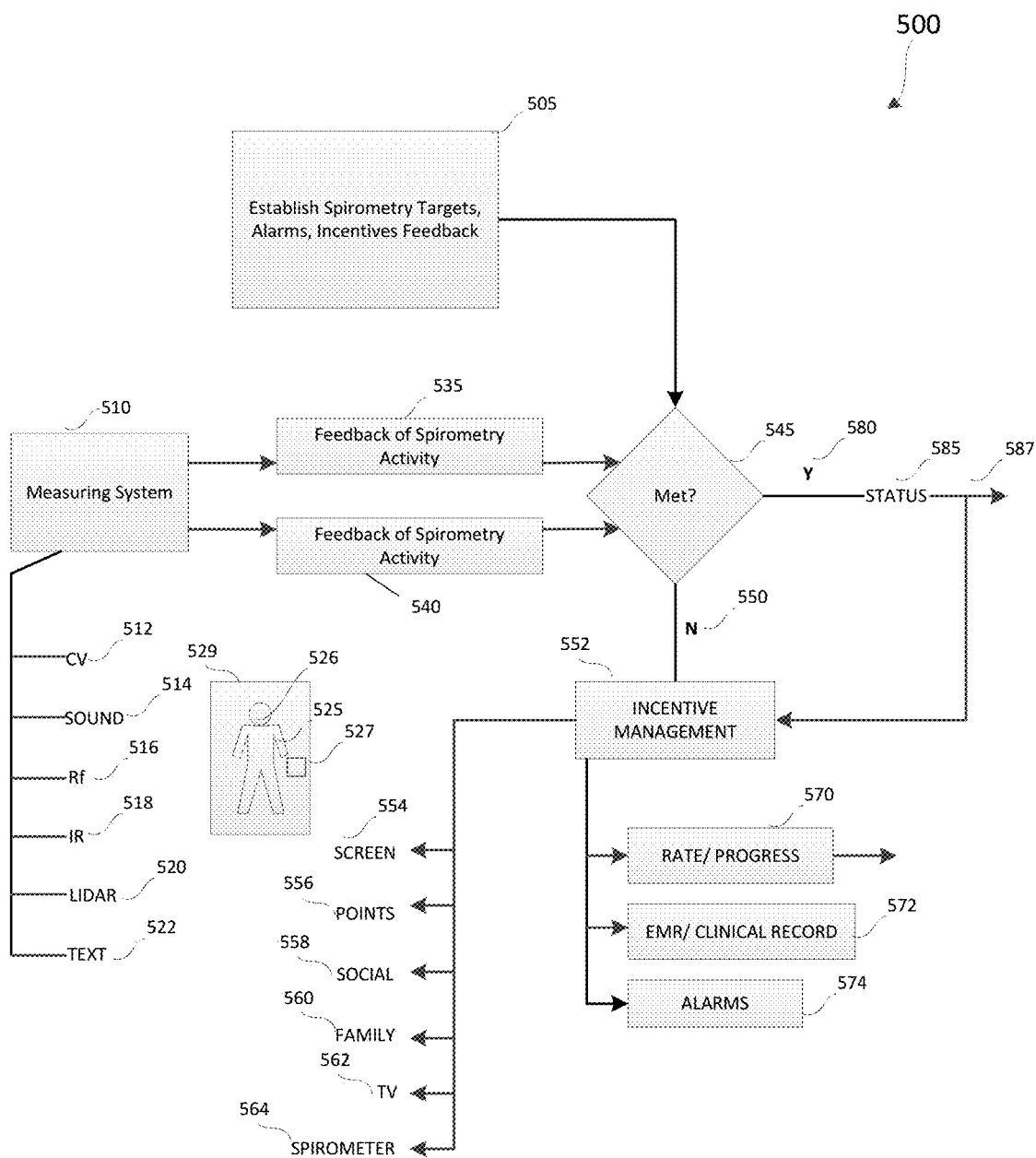
FIG. 5 illustrates an example system to measure and provide spirometry feedback.

A hospital may not have the disclosed system installed for every bed. In such instances, at block 450, assignment of patients, care providers and systems may be made to help attain improved or maximum clinical outcomes for the patients in the hospital at that time. Patients are, in such instances, assigned a room, device(s), decision support configuration(s) to help enable the hospital, with the resources of assets and personnel, deliver care to patients in the best way feasible. An assignment algorithm which serves to direct which patient receives the benefits of the disclosed installed system may be an optimization or improvement using mathematical programming, heuristics, and/or machine learning and is invoked as are the other decisions 400 from the sensing, analytic, computing and information system disclosed. Certain examples provide algorithms such as machine learning, heuristics, mathematical programing, example based evidentiary reasoning or rules within the decision support logic to assign spirometry frequency target, intensity, match of protocol to patient, risk classifier, alarm and escalation points, incentive set points, workflow triggers, assignment of patients to monitored beds and staffing coverage, etc., Data feedback can then be collected using the established spirometry targets, alarm, and incentive feedback set points established in the example method 400. As shown in the example system and data flow 500 of FIG. 5, a set of targets 505 is input for sensing and feedback. The set of targets 505 (e.g., spirometry target(s), alarm(s), incentive(s), feedback, etc.) can be generated using the example method 400, for example. Collected "as-is" data can be compared to these targets, and alarm(s) and/or feedback element(s) can be triggered accordingly.

A patient's use of a spirometer and a quality of the spirometry event is detected with a measuring system 510 which includes any one or a combination of computer vision 512, sound 514, radio frequency enabled sensor and communications system 516, infrared enabled sensing and communication system 518, ranging radar 520 or textual data or freeform unstructured input from any source 522.

Rather than using mechanical friction tabs to indicate a maximum level or rate of spirometry, optical sensing of the spirometry event enables improved accuracy, ease of use, level/rate determination, as well as a quantification of the physical activity of spirometry. This optical sensing capability builds on the art disclosed in U.S. Patent Application Publication Number 20090089093, "System and Method to Manage Delivery of Healthcare to a Patient", which uses optical sensing for surgical site infection reduction, and which is herein incorporated by reference in its entirety.

By providing a plurality of optical sensors positioned throughout a room, spatial differentiation and occluded scenes of interest cause by interruptions in line of site may be overcome. As such, a number of sensors can be used to establish a continuous line of sight and robust tracking of patients, caregivers, and objects within the patient's room. Accordingly, any desired level of optical precision to discern objects or attributes of the objects may be accommodated.

According to one embodiment, optical sensor 105 is adjustable such that it may be directed in various directions. As one example, the direction of adjustable sensor 105 is a pantel-zoom camera and is controlled by pantel-zoom manipulation by reasoning logic in which the degree of certainty of the state space is not as high as desired and a level of certainty on determination is higher. The set point level of desired precision itself may be adjustable based upon the patterns or instantaneous state of the monitored entities and events.

The use of optical sensor to locate and/or identify people, objects, and motion may beneficially replace or augment other location sensing apparatus such as RFID, Doppler, light detection and ranging (LIDAR), and/or infrared. The optical sensing may be in the visible and/or invisible light range such as, for example, near IR. A sensing device may be a pixilating device, such as, for example, a video camera or a three dimensional (3D) radar device producing direct vector length outputs. According to one embodiment, range radar and/or lidar signals may be used in conjunction with computer vision systems to acquire positional information in low light environments.

In addition, the optical sensing may be used to adjust the light levels in the room sufficient to achieve requisite illumination for detection. The same system may be used to adjust lighting levels on an ongoing basis such as, for example, energy reduction when ambient lighting levels from windows provide light or in response to a command to lower energy consumption. Further, therapeutic uses of light color, level, or patterns may also be controlled by the sensing system in an adaptive way, in response to a protocol or set point or response of the patient.

A patient 525 is observed using one or more optical sensors and located within a care context (e.g., a hospital bed 529), reconciling the actual contact surfaces of the people and apparatus with respect to each other with the multiple sensors. A spirometer 527 is located within that context 529 and within a reachable dimension of the patient 525. Should the spirometer not be adjacent to the patient, an alarm point is set for potential triggering of a positioning workflow. In certain examples, the patient's mouth 526 is located by the optical sensing system.

Feedback derived from the measuring system 510 to characterize spirometry activity 535 is made available to a comparator 545 of targets 205 to as-is frequency of spirometry for comparison to a desired pattern 430. Feedback derived for spirometry quality 540 is made available to the comparator 545 of targets 435.

Using various discrete sensors, such as camera, video, infrared, load cells, telemetry, and data from adjacent systems, etc., raw observations can be transformed into context definition of what is transpiring in the monitored environment. By comparing what is occurring to what is desired to occur (e.g., the monitored state with the desired state), anomalies are produced that indicate a deviation from what is desired. These anomalies may or may not be acted upon. The beneficial logic of the disclosed system determines which anomalous behavior can or should be acted upon by those directed to or are able to act (e.g., patients who warrant special or heightened attention due to their non-compliance with spirometry protocol).

Over a number of observations, patterns emerge that can be used to beneficially inform stakeholders in the monitored process. For example, patterns may be used for positive reinforcement or to help highlight specific areas and contexts where task execution enhancement will better achieve the desired states of the system. Adherence to protocol may be achieved by the stakeholders in the processes of care choosing themselves to personally and closely follow guidelines or adherence to protocol. This may be achieved as a result of the provided in-situ feedback alerting a stakeholder of a variance to which they would respond appropriately to (or have performance consequences) and/or the provided objective feedback. By informing stakeholders of these patterns, stakeholders are encouraged to proactively change their behavior in such a way as to avoid the anomaly all together. Accordingly the observations may be used to transform stakeholder behavior in such a way as to avoid having protocol violations or adverse states of the system.

The comparator 545 of protocol set points to an actual pattern and comparative quality of the spirometry event can be implemented using a rule engine, a case based reasoning engine, an example-based evidentiary reasoning engine, a fuzzy logic reasoning engine, and/or a statistical or machine learning derived function, for example. Should the "as-is" information meet the targeted goals for that point in time, an in compliance state is "yes" 580 and is made available for updates 585 in systems such as EMR, clinical workflow, Safety and Capacity Command Center, incentive cohort systems, etc. An incentive cohort management system 552 appropriately updates feedback loops to maintain positive reinforcement. Targets not being met 550 likewise trigger the incentive management system 552 so as to engage 445, per the escalation set points 440, the cohorts available into the patient's motivations (or lack of) with the intent of the patient deciding to comply with the protocol.

Feedback mechanisms are controlled by the incentive management engine 552 and can include, for example, a video screen 554 located in view of the patient 525 which is configurable to remind the patient of the protocol and to provide feedback and incentives, incentive points 556 awarded or subtracted as a function of protocol compliance, social media form factors 558 such as Facebook™, personal web pages, Twitter™, Pinterest™ and/or other sites or systems whose inputs can include a numerical value or de-identified image that corresponds to the patient's 525 progress, family notification or log on status updates 560, content served via the in room television or video monitor 562 that is appropriate to incentivize the patient using methods disclosed in U.S. Patent Application Publication Number 20080146888, "System and Method for In-situ Mental Health Monitoring and Therapy Administration", which is herein incorporated by reference in its entirety, and spirometry device interactivity 564 wherein physical apparatus can be dynamically updated to change color, make a noise, vibrate or have an update to an embedded screen, for example.

The incentive management system 552 also interfaces with other systems by publishing indicators or actual metrics for rate of spirometry compliance and actual measures 570, writing to the EMR and clinical record managed by care providers 572 and alarm set points that trigger workflows 574.

Mechanical feedback of incentive spirometers enables patients to have direct feedback. In combination with the patients' own internal motivations, feedback enables them to work their breathing pressure and volume. However, an aid for actually choosing to do the spirometry procedure is missing. Also missing are exogenous incentives beyond the patients themselves or their care providers. Certain examples overcome both limitations in spirometry by reminding patients who need to be reminded as to what the protocol is and by enabling a sense of community, support or competition—whichever or whatever combination increases the patient's participation in the protocol.

Figure 6:
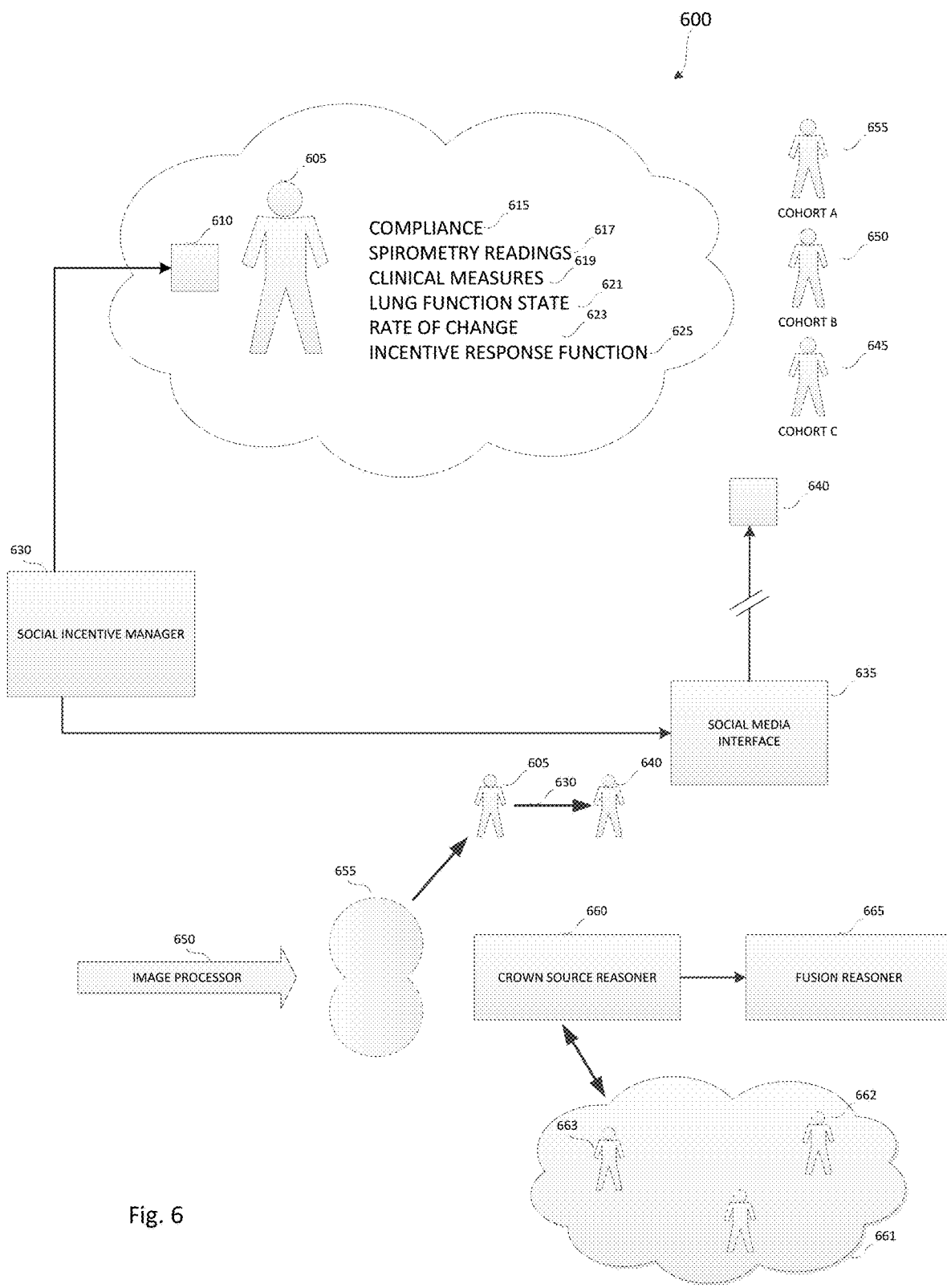
FIG. 6 illustrates an example system to determine and provide social incentives for spirometry facilitated lung function improvement.

Aspects of this social incentive for spirometry facilitated lung function improvement are depicted in FIG. 6. The example system 600 includes metrics, a social incentive manager 630, social media 635 and cohort(s) of others who may be able to engage the patient 605 and positively reinforce whatever native incentives and self-discipline the patient 605 has.

The patient 605 is monitored 500, and an interface 610 is provided in the form of a video terminal, a smart phone, the spirometer itself, a nurse call handset, television or other device that enables the receipt of text, graphics or video from others that is managed by the social incentive manager engine 630. In an example, the patient 605 is provided feedback regarding elements of compliance to a scheduled protocol activity 615, readings from the spirometer 617, targeted clinical measures 619, lung function state or status 621, rate of change of an aspect of protocol compliance, breath frequency, volume, rate or lung function 623, and an incentive interaction and response from cohorts who have been selected 625 for various aspects of comparison and support. Each of these aspects 615-625 is configurable on the interface device(s) 610 used and may show, as selected, both a current measure and a target or gap to the target, or icon or color representing a degree to which what is being measured meets its target.

In the example of FIG. 6, the social incentive manager 630 manages rendering of graphics, text and content exposed to the patient 605 via interfaces 610. The social incentive manager 630 is also configured to selectively feed inputs and outputs to interchange mediums such as other similar patients on the system within a given hospital or an interconnected set of hospitals using the system. Additionally, social media interface(s) 635 can be used to engage other cohorts of patients, former patients, friends, family, other persons with an interest, etc. In certain examples, interfaces 635 include gateways to Facebook™, Twitter™, Pinterest™, Snapchat™, personal web pages, blogs and websites of various origins and intent, etc. Information leaving the social incentive manager 635 is appropriately anonymized such that no image or personally identifiable medical information is allowed out without proper compliance and privacy considerations observed. Where social media is used among known persons who have a specific relationship with the patient, the disclosed system exposes the patient's name and appropriate metrics and performance gaps, if any, and incentive points. An alarm may be posted or a rate of change detected wherein positive reinforcement may help the patient to work harder at breathing exercises, for example.

Cohorts may be defined by different features. Other patients in the same hospital can, in one example, be 'Cohort A' 655 who are grouped into a meaningful context. One example is all persons using spirometry, and the goal is to have that patient population try to collectively, for example, meet a spirometry activity goal. The feedback can be from each patient with respect their individual protocols and the gaps aggregated, for example. Those patients whose use of spirometry is low relative to their protocol or the global objective or minimal threshold are identified for the clinical staff for intervention by care providers and de-identified for others in the cohort but made available by nickname for the purposes of others sending them well wishes, encouragement, or targeted feedback, for example.

Another cohort B 650, in an example, may be friends and family who subscribe to Facebook™. The patient's points or progress is posted at a milestone or points of the day or achievement of a given volume or rate or compliance. Persons in that cohort 650 then respond with encouraging words, "comments" or "likes" so as to keep the patient's spirits up and progress going.

Another cohort C 645, in an example, may be persons in the population of people online who seek out to be encouraging or may incorporate the patient into another gaming or incentive mechanism—such as a financial incentive to be given to a charity if a certain progress is made for one or more patients, or a betting pool or prayer group. The varied reasons for interest and incentive mechanisms are too numerous to tabulate, but the example system 600 enables protection of specific patient identity and enables interactivity, as appropriate. An interaction mechanism 640 for the cohorts 645, 650, 655 is varied—such as a computer, smart phone, text, etc.

In certain examples, a patient image can be de-identified 655 using an image processor 650 to remove facial features and publishing an outline, avatar, or comic caricature which may in turn be used by the social incentive manager 630 for directed promulgation to cohorts such as exposed by 640 or amongst cohorts 645, 650, 655. The image processor 650 can use computer vision to generate a shape classifier using optical sensing information, for example.

A computer vision system, which includes one or more sensors, is utilized to acquire images that are then reasoned over to ascertain what the objects are in those images. The computer vision system transforms the representation into mathematical vector space where in those vectors are transformed into positional meaning, such as the location of a person. Thus, objects may be ascertained without a physical reproduction or display of an image.

A patient may be subscribed and/or self-select his or her incentive cohort(s) 645, 650, 655. Cohorts 645, 650, 655 may be selectively engaged by the system so as to offer the ideal incentive a given time. There may be blended scores, blended cohorts, etc.

Sensing the proper use of a spirometer is a function of sensors and reasoners. Certain examples advance the current art dramatically with optical sensing and enable development of reasoning engines by an original equipment manufacturer as well as crowd sourced persons who, when presented with feature sets, response variables and objectives, can develop and implement a decision support algorithm 440, 445, 450, 510, 552, 574, 615, 621, 625 or the logic of cohort interaction 640 to be hosted by the system's servers or remotely hosted and fed information so as to receive a decision or characterization by remote algorithm.

Certain examples provide relational algorithms such as regression, neural nets and machine learning involving feature set and output determination hosted by a crown source reasoner 660 which facilitates participation of algorithm developers 661, 662 and 663 to create their own decision support engines that can be then used by the system 600 individually or as a portfolio in the fusion reasoner 665.

Figure 7:
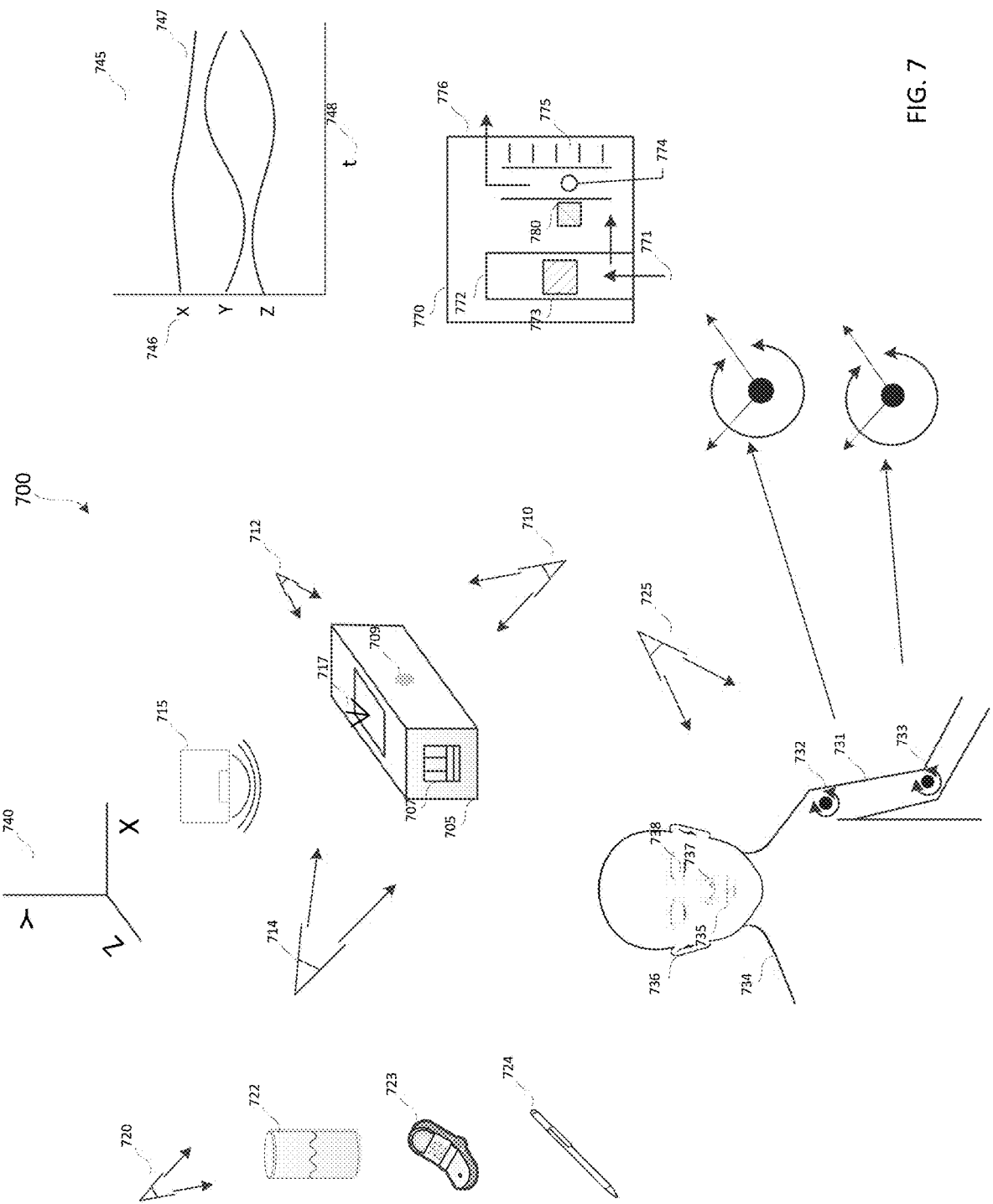
FIG. 7 depicts an example system for identification, classification, orientation and crowd sourced reasoning augmentation.

FIG. 7 shows an example system 700 for identification, classification, orientation and crowd sourced augmentation.

A spirometer 705 is a physical device in one embodiment of the invention that is located within reach of the patient 730. In certain examples, optical tags or markings 707 are positioned on the spirometer device 705 in a pattern set to align with a physical orientation of the device 705. In another example, optical tags or marking 707 are arranged in a pattern which is reflective when illuminated in near infrared (IR) light and whose orientation enables resolution of the device's 705 physical position. In another example, an RFID or passive tag or active tag 717 is triggered when in the presence of a triggering mechanism 715. The trigger 715 may also include a wireless transmitter to transmit information to/from the spirometry device 705. The tags 707 and 709 may also be unique identifiers to device 705.

The spirometry device 705 is observed optically via fixed image or a frame rate sequence such as from a video camera 710, 712, 714 with the cameras and/or optical sensors being fixed or mobile such as on a smart phone. Objects 720 in the vicinity of the patient 730 can also be observed. For example, objects of interest may include a water glass 722, phone 723, writing instrument 724, and/or other items of clinical or operational interest. These items may be recognized by shape classifiers used in the art of computer vision or may be tagged 707, 709 as the spirometer 705 may be. The system differentiates between the spirometer 705 and other object that the patient may use based on its shape, markings, and/or associated devices, for example.

In one example of the system 700, a distance 727 between the spirometer 705 at point 726 and the patient's head or mouth 735 at point 728 may be specified as feasible to allow spirometry. The system 700 triggers an alarm when the spirometer 705 is not within reach, for example. For example, when the spirometer 705 has fallen out of bed and the bed rails are raised because the patient is a fall risk, the patient 730 is prevented from accessing the spirometry device 705, and an alarm is triggered.

The patient 730 performs spirometry by placing his or her mouth 735 over the blow tube of the spirometer 705 and respirating. This action is sensed by optical sensors 725, that may be the same sensors 710, 712, 714 as those used to track the device 705. In an example, orientation of the spirometer 705 may be checked against the orientation of the patient's head 730 in X, Y and Z planes 740, using the shape of the spirometer 705 or the tags 707, 709 or a gyrometer 717 attached to the spirometer 705. Orientation of the patient 730 is determined by shape classification of the head using any one or combination of features such as ears 736, nose 737, scalp, eyes 738, shoulders or neck 734. In an example, it is determined that spirometry has occurred if the device 705 has met the mouth 735 for a duration and its path from its former resting position 527 on the bed 529 is articulated through a consistent logical arc and motion queues of the shoulder 732, arm 731 and elbow or wrist 733.

In certain examples, a relationship 745 of orientation 740 over time based on optical sensing can be derived based on relative changes in the XYZ locations 746 of tag 707,709 patterns 747 over time 748.

Additionally, sensing of a spirometry result 770 may be optical or provided by a radio frequency (RF) system 717, 715. A patient's respiration moves air 771 in a chamber 772, which displaces a piston 773 due to differential pressure. Air volume is measured by a sensor 780 or optical sensing of the piston's 773 movement relative to the cylinder 772, both of which can be tagged for optical pickup. Air volumetric rate is determined by displacement of an object 774 in the air path of a measured volume 775 and then discharged 776. The rate is optically observed by the orientation of the flow object 774 and gradients 775 corresponding to air velocity or is observed by an RF enabled sensor 780, for example.

As an example, the measured volume and or rate is achieved by a patient per a frequency setpoint specified by the selected protocol. However, suppose measures of airflow are below those setpoint(s). In an optical sensor example, these measures are derived from observation of dynamic spirometer piston position relative to a static mark on the spirometer and processed to calculate a measurement to which those distances correspond. In an example in which a sensor is joined to the spirometer, a capacitive distance estimation or light gauge or other displacement sensor creates a signal corresponding to volume or rate and broadcasts that result to a base station via WiFi, RF or IR pattern. The disclosed system's logical elements then provide feedback to the patient on the spirometer device, on the patient room video screen(s), into the medical information system(s) and, if configured, to the configured or algorithmically chosen cohort(s) so as to activate the social media feedback for incentive purposes. If, despite the self and cohort feedback, the patient is still not meeting breathing quality goals, or if the patient lags on performing the protocol itself, the hospital staff is notified by the system's logic to investigate. In certain examples, a beneficial advantage to the hospital staff is that only those patients who are lagging behind in adherence or performance are actively engaged person to person, thus saving interruptions for the patient and productivity for the staff.

Thus, certain examples provide an incentive to a patient via a user interface with metrics comparing their actual spirometry with the spirometry specified by their assigned protocol. Certain examples provide spirometry incentive feedback to an EMR and/or other system. Certain examples provide spirometry incentive feedback to designated patient stakeholders, such as family and friends. Certain examples provide spirometry incentive feedback to a pool of other patients who are appropriate peers and provide that cohort with social incentives/friendly competition to help increase compliance to desired protocol and raise compliance of the cohort. Certain examples provide a mechanism for feedback to members of the incentive cohort who are not doing as well so as to enable social connection and positive incentive.

Figure 8:
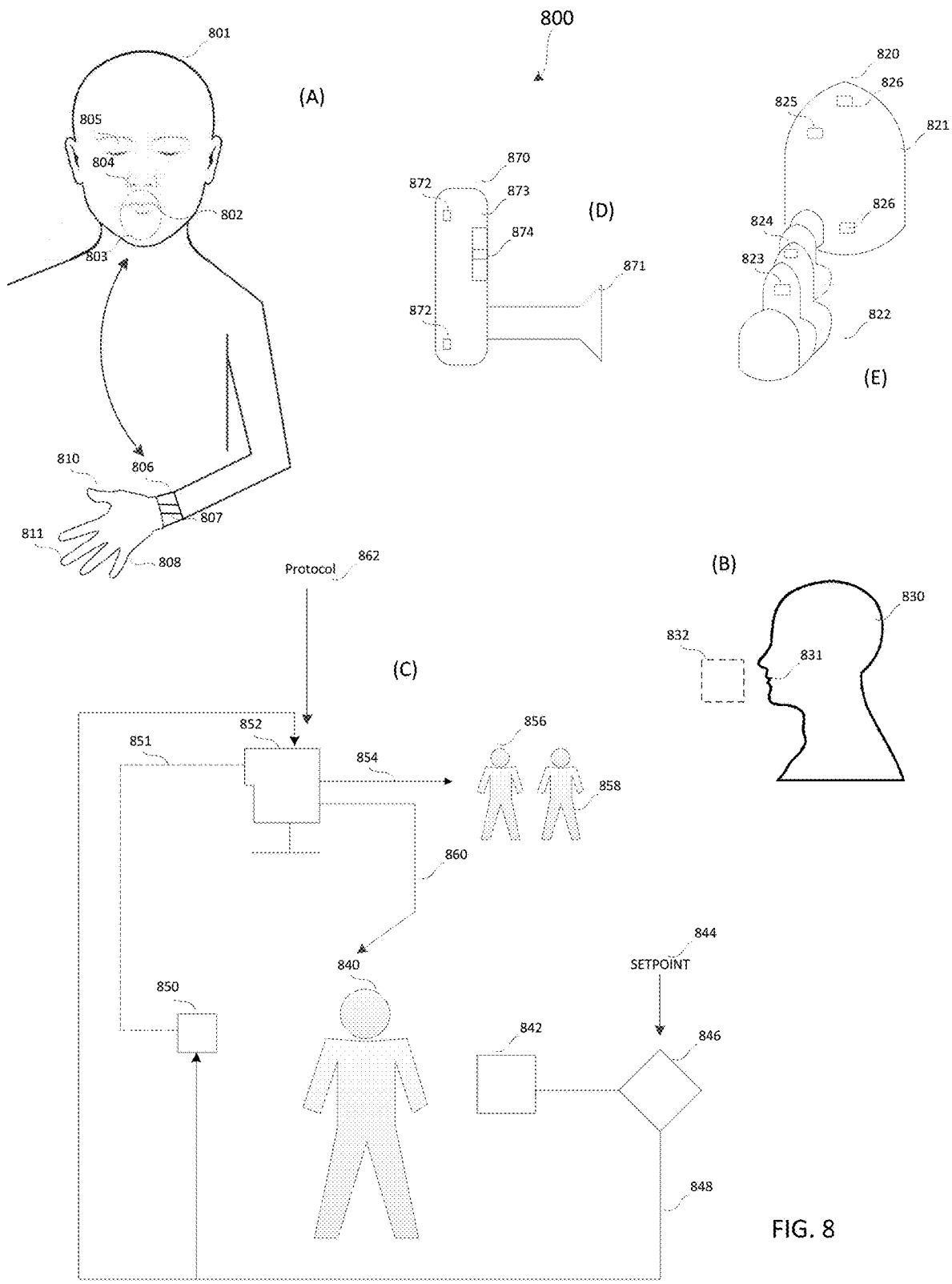
FIG. 8 depicts an example system for ventilator and spirometry interactions with facial-oral structure of a patient's head.

FIG. 8 depicts an example system 800 for ventilator and spirometry interactions with the facial-oral structure of a patient's head. As shown in the example of FIG. 8, interactive control of a clinical apparatus interfacing with a human mouth can be facilitated.

In certain protocols, specific actions related to clinical devices, such as respirators and spirometers that interact with the head and/or mouth, are controlled to sustain a clinically effective orientation, usage, and limit contamination from biological growth such as bacteria, for example.

In an example, a clinical device is controlled with respect to a patient who effectively is immobile for medical or mental acuity and cannot aid in their own care. In another example, the clinical device is controlled with respect to patients who are able to be and are integral to their own medical care yet have different levels of capability or willingness, such as in the presence of pain.

In both circumstances, in which a patient is not able to orient and use a device and in which a patient is able to orient and use the device but requires guidance or motivation to do so, the clinical device must be properly controlled over a sustained interval of time (e.g., days, weeks, months, etc.) such that it is unrealistic for a single other individual to track and intervene in the physical delivery of care. Lack of physical delivery of proper use as specified in medical protocols can result in patient harm that spans a continuum from slower recovery to an acquired pneumonia to increased chances of death.

The example system 800 helps to aide in physical orientation and use of clinical devices with respect to a patient's mouth. Section (A) of the example of FIG. 8 shows a human head 801 with its features such as orientation of mouth 802, nose 804, eyes 805 and an intended location 803 of a clinical device (e.g., spirometer, ventilator, oxygen mask, etc.) with respect to these features. In certain examples, use of the device may be tailored by a care provider to a particular patient so as to achieve a measured medical result such as level of blood oxygen or rate of air movement with a patient's lung function. The patient may be tagged 806 with an identification device 807 that is a symbol, text, optical pattern, RFID, bracelet, temporary tattoo, and/or other unique identification device. The patient may be identified by an automated reasoning system which computes facial features 801, 802, 804 and 805 for example. A specific patient, with a medical protocol, is identified.

As illustrated in section (A) of the example of FIG. 8, a patient's hand(s) 808 and fingers 810, 811 hold and orient the clinical device(s) and move 812 them to a facial location 803, such as the mouth and nose as needed for the use of the device.

In certain examples, a clinical device such as a ventilator tube or oxygen mask 832 (shown, for example, in section (B) of FIG. 8) is positioned on a patient's head 830, 801 to interact with the mouth 831, 802 in a specified duration or pattern or in a dynamic pattern that results from the closed loop feedback of a biometrical indicator such as blood oxygen level.

As illustrated in section (C) of the example of FIG. 8, a patient 840, whose biometrical indication and physical orientation of apparatus may be or is being controlled, is monitored at block 842 with a clinical device such as a blood oxygen sensor and compared to a desired setpoint state 844 at a particular point in time (e.g., at the instant of measurement) and/or over an interval of time 846. Feedback 848 proportional to a gap in actual 842 biometrical indication with respect to the desired level or setpoint 844 is caused by diminished lung function of the patient, for example, in the embodiment of FIG. 8.

A controlled clinical device 850, such as a spirometer, an oxygen mask or ventilator is monitored 851 by a disclosed protocol detection and control system 852 that compares physical use of the device 850 with an associated protocol 862 for its physical use and/or indicator of effectiveness with respect to the patient's medical care. Specific personnel direction may be given to individuals 856, 858 in the context of their workflows when the protocol 862 has a lapse or out of range signal 854 at a particular time and/or through an interval of time in the past and/or forecasted interval in the future. Specific interaction 860 may be provided to the patient 840 with respect to physically orienting or using the device 850 and/or receiving feedback from others 856, 858 who may be care providers or other persons who monitor or advise or coach or provide motivation to the patient so as to keep the delivery of care within protocol specification 844, 862.

The device being controlled 832, 850 may be, for example, an incentive spirometer 870. As shown in section (D) of the example of FIG. 8, a mouth piece 871 of the incentive spirometer 870 is designed to be contained by the patient's mouth 802, 831 in use as the patient exhales, thus pushing a volume of air from the patient's lungs through a measuring channel 873 which has an indication of flow 874 that can be monitored as a clinical indicator 842. The spirometer 870 is physically oriented 812, 803 by the patient 801, 830, 840 for the device 870 to function properly. Optical indicators and features 872 on the device 870, 850, 832 are used by the control system 852 monitor and detect device orientation with respect to the mouth and/or other facial feature(s).

The device being controlled 832, 850 may be, in another example, an oxygen mask with markings that can be optically sensed.

The device being controlled 832, 850 may be, in another example, a ventilator interface 820 for a patient. As shown in section (E) of the example of FIG. 8, the ventilator interface 820 includes a tube 822 and mouthpiece 821. The tube 822 is marked with one or more optical indicators 823, 824 which are unique to that tube 822 and serve not only for orientation detection 851 by the system 852, but also as a unique serial number. The tags 823, 824 may be visible to the human eye or via a detector in the infrared or other non-visible range. The tube 822 and mask or any other component of the clinical device 820 may also be tagged with RFID or other unique identifier 825. The mouth piece or mask 821 is tagged 826 with optical indicators or sensors to likewise orient its position by the system's detection and logic 852 on an absolute geometrical space or relative to specific features 802, 804, 805 of the patient.

The example system 800 can be applied to a variety of example clinical devices. A first example clinical device is incentive spirometry for patients who are able to control the use of the clinical device but may benefit from the monitoring and help of others. A second example clinical device is a ventilator for a patient who is effectively unable to self-manage. A third example clinical device is an oxygen mask, operation of which may be managed by a patient and/or a care provider. As disclosed above, the spirometer, ventilator, oxygen mask, and/or other lung function-associated device can be controlled by the disclosed system 800.

Certain examples help improve participation rate and quality of self-incentivized protocol adherence such as spirometry with a closed loop monitoring method, set point selection, feedback and social reinforcement.

Certain medical protocols are specified in a patient's care plan to help them heal and/or lower a risk of an adverse condition developing, such as ventilator-acquired pneumonia. These protocols are successful if appropriately chosen for a patient's specific condition, and if the patient actually performs the prescribed actions.

In many cases, these protocols, when performed, create discomfort and, therefore, a disincentive to perform the protocols. Through example systems and methods disclosed herein, providing goals and measurement indicators as feedback create an incentive to reach a goal and help offset a human tendency to reduce or minimize actions creating discomfort.

The goals are static in nature, only updated in period fashion as a patient's progress can be considered because it is hard to determine the actual rate of progress and there is no practical means to record and then analyze the performance of the prescribed activity or the quality or measure of the activity. Dynamic goals which pace just far enough ahead of a patient's current ability in order to accelerate capability are not possible for lack of measures in both dimensions of activity and quality.

Care compliance is typically a self-regulated regime as it would be cost prohibitive to have human monitoring and recording of data. Typically, humans respond to encouragement to augment their own internal motivations. In considering a protocol that creates discomfort, occurs predominantly in isolation, includes an easily forgotten schedule, and has a rate of progress/goals that may not be known, certain disclosed systems and methods realize improved medical outcomes that otherwise cannot be realized in the current art.

Reasoning algorithms in clinical decision support have historically been forward or reverse chaining if-then-else triggers as to a person's compliance to or progress from a protocol. This if-then-else limitation occurs due to episodic charting and low gauge repeatability and reliability of recorded measures for the protocol. In contrast, certain examples utilize machine learning to train over an enhanced feature space to characterize a system state with a high degree of precision. A diversity of algorithms, each constructed with different feature selection and method, describe the observed in a diverse way. A multitude of these diverse models can increase the specificity of a detection by creating ever more nuanced and specific activity detection as well as acting as a confidence enhancement for the automated detection of the same activity with multiple reasoning engines whose outputs are fused.

Certain examples address a need for enhancing lung function in hospitalized patients, many of whom have had surgery in the chest cavity with general anesthesia and are oriented in a bed. These patients are at risk of fluid buildup and decreased lung function as the alveoli sacks are not opened up without backpressure. An incentive spirometry protocol can be prescribed so as to create opportunities for that requisite back pressure. The patient is given volume and rate feedback from the mechanical device. Care providers compare an observed volume and rate to a prescribed goal and chart the status. The patient is instructed to use the spirometer for, as an example, ten breaths every hour, to breathe in slowly at a goal rate to achieve a goal volume of air and to exhale at a goal rate to achieve a backpressure. The nurse may make rounds every several hours and, thus, it is up to the patient to execute this protocol.

Certain examples overcome protocol oversight limitations with a protocol selection, standoff optical measuring system, reasoning system, automated data source for charting, and dynamic feedback for the patient to both remind them to use the device and their progress and to engage social incentives from patient stakeholders who could be cohorts also in a given hospital or a network of hospitals or a social network. Enabling social participation while also maintaining anonymity and discretion is facilitated using a rendering capability which captures the form of a person's activity and projects it, if chosen to, in outline or comic format. A lack of ability for human witness of the protocol for compliance is overcome with an alerting system to focus staff interventions for patient coaching. Further, detection algorithms can be developed using an enhanced feature space data set with anonymized patient information.

In certain examples, while the need for improved lung function may be desired for patients after surgery and a general prescription may be made, the specific targets of lung volume, flow rate and spirometry patterns and patient incentives have an opportunity for specific customization and goal setting.

Certain examples provide a mechanism for feedback to care providers with respect to quality of delivered care as measured by compliance to a specified protocol. Specifically, for example, feedback can be provided in control of ventilator and patient interactions. Care provider feedback may be with respect to a targeted level of protocol fulfilment and/or comparatively to other care providers with similar patients, thereby also benefiting from incentives of being "better" or reducing occurrence of being "worse".

For example, a score, color (e.g., red, yellow, or green light), family notification, point accumulation/deduction, comparison, etc., can serve to provide feedback and re-enforce incentives to comply with the spirometry protocol.

Additionally, certain examples provide for an alert or alarm to a care provider (e.g., a doctor, nurse, etc.) to respond to, monitor, and/or otherwise care for patient(s) who have worse than a threshold compliance. Certain examples can identify a subset of patients warranting additional attention, guidance, care, etc.

Certain examples compare patient specific occurrence metrics for incentive spirometry or ventilator-patient setup and maxiofacial procedure collected through computer vision (CV) algorithms with existence of spirometry or VAP order sets and/or the occurrence of surgical anesthesia levels above a triggering threshold to determine significant occurrence of non-compliance with the protocol.

Certain examples provide an ability to customize a spirometry or VAP protocol sequence or measure of activity and or consumable consumption (e.g., tubing, etc.) for a specific patient over a given interval of time and/or in response to other triggering event(s) or clinical measure(s).

Certain examples detect a shape of the spirometer or VAP from N aspect angles with multiple optical inputs from individual still images and/or streaming video. Individual signals are jointly processed to build a composite three dimensional volumetric expression for a given instant or over time. Certain examples detect a location of the spirometer or ventilator with respect to a patient's mouth using an optical tag sensed by the optical input in still and/or streaming video. The optical tag may be passive, for example. Each tag can include a generic spirometer or ventilator mask identification (ID) pattern and/or a unique specific spirometer or ventilator or tube pattern, for example.

Certain examples detect a location of the spirometer or ventilator mask or tube using an optical tag with an oriented pattern corresponding to the spirometer's or mask's or tube's orientation in XYZ space, sensed by the one or more optical input in still and/or streaming video signal inputs, reconciled in one or multiple planes. The optical tag can be passive, for example, and each tag includes a generic spirometer or ventilator mask or tube or other device for the delivery of care such as a toothbrush or a lip balm, ID pattern and/or a unique specific spirometer or other asset's pattern.

Certain examples detect a location of the spirometer or ventilator associated asset such as tubing or a consumable using an active optical tag emitting visible or IR light in a broad unstructured emission pattern that may be sensed by the optical input in still and/or streaming video. Each tag includes a generic spirometer or ventilator or consumable ID pattern and/or a unique specific spirometer or ventilator associated asset in the delivery of care pattern, for example.

Certain examples detect a location of the spirometer or ventilator associated asset using an active optical tag emitting visible or IR light in a structured emission pattern that is sensed by the optical input in still and/or streaming video to orient the position of the spirometer in addition to its XYZ location. Each tag has a generic ID pattern and/or a unique specific device pattern, for example.

Certain examples detect a location of the spirometer or ventilator associated asset or consumable in XY, XYZ and XYZ+time.

Certain examples train shape detection algorithms for spirometer(s) or ventilator related assets from one or more training examples in-situ and in mock up.

Certain examples detect patient face and facial surface construction and orientation with optical inputs from still images and/or streaming video from one or multiple inputs. Certain examples detect a location of a patient's face with optical input in still and/or streaming video and calculate a distance of the spirometer or ventilator mask with respect to the detected face/mouth position. Certain examples detect a location of the patient's face with range radar/lidar input and calculate a distance of the spirometer or ventilator related asset with respect to the detected face/mouth position, making an automated feedback signal directly correlated to the fit of the spirometry device in a patient's mouth or a ventilator mask on a person's facial structure.

Certain examples detect a location of the spirometer, tube, toothbrush, oral care product or ventilator mask using RFID and/or other tag-based sensor.

Certain examples detect an orientation of the patient's face using facial features using optical input in still or streaming video from one or multiple input signals. Certain examples compare the orientation of a patient's face and the orientation of the spirometer or mask, creating a metric of joint alignment correlated to the appropriate use of the spirometer or mask. The absence of a fit between spirometer or mask and face and with a range of orientations provides a "mask off" indication of, for example, a "sedation vacation" or period when the patient is ideally respirating under their own lung function per the protocol.

Certain examples calculate motion queues of articulating body parts such as arms, legs, head, neck, torso using optical and/or range radar, and use the motion queues as a component of a reasoning algorithm to track a spirometer's position relative to a patient's face or the management of oral care in the case of a ventilator such as brushing teeth, applying balm, etc.

Certain examples calculate compliance to protocol for one or a population of patients, and prioritize for which patients to provide which clinical services to so that compliance is increased to a specified threshold and to trigger specific clinical workflows based on compliance.

Certain examples calculate compliance with a protocol for one or a population of care providers, and prioritize for which patients to provide which clinical services to so that compliance is increased to a specified threshold. Certain examples trigger specific clinical workflows based on compliance.

Certain examples collate outcomes of patients who use the system for incentive spirometry and compare those outcomes to a frequency of spirometry, providing an analysis by appropriate cohort.

Certain examples collate outcomes of patients who use the system for ventilation and compare those outcomes to a frequency of ventilation, tube changes, oral care, self breathing, etc., thereby providing an analysis by appropriate cohort.

For example, in the case of spirometry, a patient lying in bed is monitored, and one or more optical sensors are used to detect that the person holds a cup of water to his or her mouth. The system evaluates the data but does not identify the cup as a spirometer. Similarly, the patient holds a phone to his or her mouth, and the system considers it and concludes it is not a spirometer. Then, the patient holds a spirometer to his or her mouth, and the system identifies it as such and begins a timer to track how long it is there. After the patient removes the spirometer from their mouth, the system flashes an indicator or message or state change in a logical engine such as "incentive spirometry has occurred with a given probability".

In certain examples, a patient in bed image is captured and automatically tagged (e.g., with metadata) for replay for the purposes of protocol feedback and/or outcomes versus protocol study. In certain examples, a patient in bed image is captured and automatically tagged with whatever information is reasoned and is then shown for human input calibration to train the recognition algorithms. In certain examples, a patient image is removed by the system and replaced with queues indicating the features of the recognized objects in the field of view. The abstraction is then presented for feedback and algorithm training purposes with input from trained staff In certain examples, the abstracted and de-identified patient view is presented to others via a web enabled portal which enables persons who wish to train the algorithms with their human input or enable other reasoners to use the image feature set or the reasoning output of other pattern recognition engines developed by others to determine the activities in the abstracted image data set and/or include the compliance of abstracted image or other reasoned outputs into the protocol adherence reasoning.

Certain examples provide an ability to fuse multiple reasoning algorithms provided by persons or mechanisms subscribing to system data sets such that the clinical system benefits from multiple inputs with respect to detection and conclusion accuracy.

Certain examples provide an ability to enable de-identified images and their incentive metrics and other reasoned outputs provided by others into a web enabled interactive environment in which persons outside of the care environment may receive updates as to a monitored patent's state or compliance and provide interactive feedback such as thumbs up, icons, written, verbal or video encouragements. In certain examples, social media modalities can be fed such metrics, incentives, feedback, etc.

Certain examples facilitate measurement of lung function readings and measurement of lung function changes. Certain examples provide prognostication of lung function states at certain times (e.g., t+N, where N is an interval or duration of time). Certain examples provide a rate of change of realized and forecasted state change for incentive feedback and population comparison either to a protocol or relative value, corrected for cohort.

A technical contribution for the disclosed methods and systems is that they provide for computer implemented systems and methods for protocol adherence closed loop control.

Figure 9:
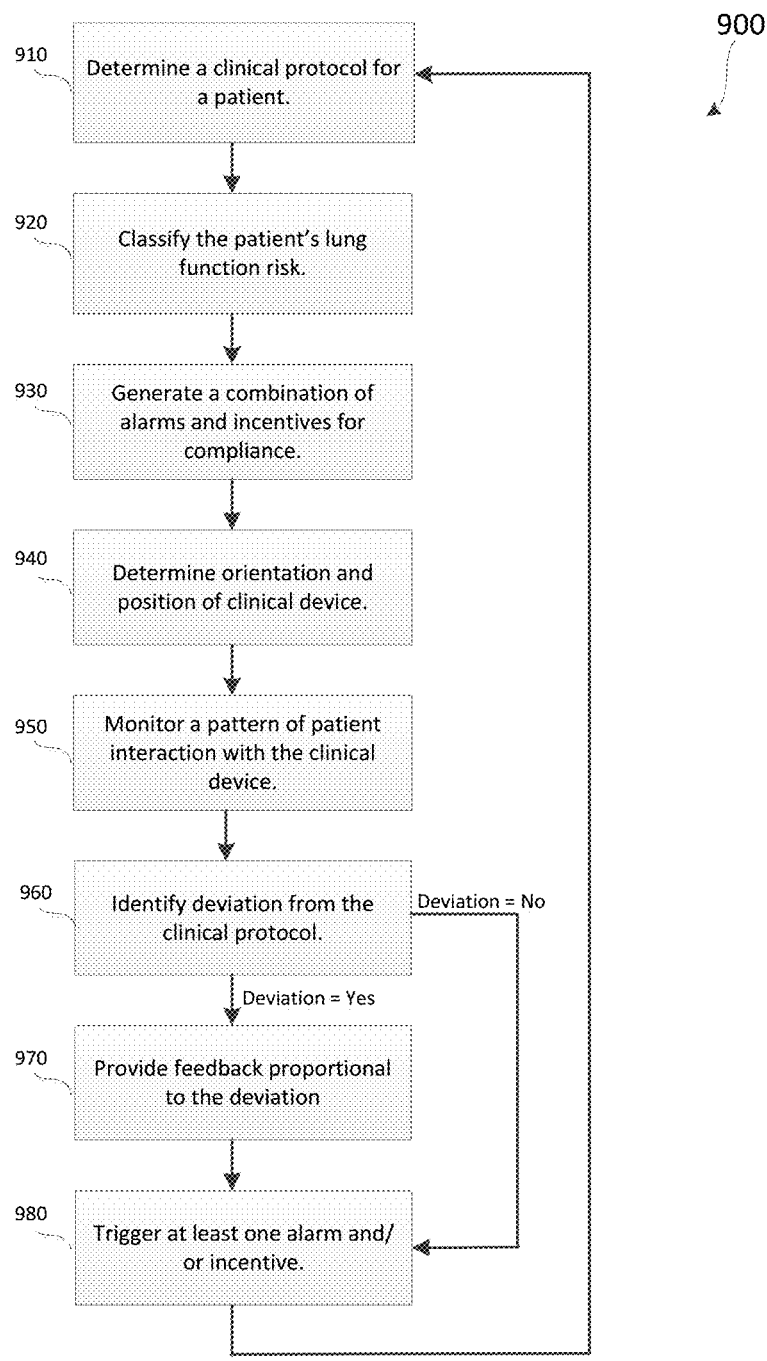
FIG. 9 illustrates a flow diagram of an example method for system-driven monitoring, analysis and feedback with respect to execution of a lung function clinical protocol.

FIG. 9 illustrates a flow diagram of an example method 900 for system-driven monitoring, analysis and feedback with respect to execution of a lung function clinical protocol (e.g., spirometry, ventilator, oxygen administration, etc.). The example method can be executed in conjunction with example systems 500-800, for example. At block 910, a clinical protocol is determined for a patient. The clinical protocol includes, for example, a series of prescribed tasks using a clinical device to address a clinical condition. For example, a spirometry protocol, ventilator-acquired pneumonia monitoring protocol, enhanced oxygen protocol, etc., is determined for a patient. The clinical protocol can include a plurality of tasks involving a plurality of devices including both clinical and non-clinical devices, for example.

At block 920, the patient's lung function risk is classified based on patient attributes and the clinical protocol. For example, patient condition, health history, medical procedure, lung capacity, lung impairment, etc., are used in combination with the determined clinical protocol to determine a risk to the patient's lung function.

At block 930, a combination of alarms and incentives for compliance with the clinical protocol are generated based on the patient attributes, clinical protocol, and the patient's lung function risk. For example, the system evaluates patient condition, limitations, other strength(s) and/or weakness(es), etc., with respect to the clinical protocol and generates a combination of alarms (e.g., triggers, alerts, messages, reports, prompts, etc.) and incentives (e.g., rewards, awards, messages, prompts, certificates, triggers, etc.) to encourage compliance with the clinical protocol.

Thus, for example, the system evaluates a spirometry protocol and generates alarms based on timing, rate, position, etc., to alert the patient and/or other personnel involved in the patient's care/support (e.g., the patient's cohort) when task(s) in the protocol are not followed, threshold(s) are not reached, deviation(s) become too large, etc. Additionally, the system generates incentives to encourage the patient (and his/her cohort) to comply with the tasks in the clinical protocol (e.g., incentive spirometry). Incentives can include awards (e.g., ribbons, badges, medals, commendations, social media activity, etc.), rewards (e.g., hospital gift certificates, additional privileges, etc.), congratulatory messages, and/or other re-enforcement for the patient to follow the clinical protocol, for example. Patient alarms and incentives can also be based on matched attributes of other patient(s) and/or additional stakeholder(s) (e.g., the patient's cohort) able and willing to engage in providing interaction and assistance with the patient and clinical protocol, for example.

At block 940, an orientation and position of the clinical device are determined with respect to the patient's head based on one or more tagged features of the clinical device compared to one more identified features of the patient's head. For example, RFID, optical, near field communication, and/or other tags/sensors can be placed on the clinical device, and position and orientation of the device can be determined using data from the tag(s)/sensor(s), taken alone or in combination with camera (e.g., still, video, infrared, etc.) information and compared to identified features of the patient's head (e.g., nose, mouth, eyes, ears, etc.) to determine an orientation and position of the clinical device with respect to the patient's head.

At block 950, a pattern of patient interaction with the clinical device is monitored based on the determined orientation and position of the clinical device with respect to the patient's head tracked over a period of time using the one or more tagged features of the clinical device compared to one or more identified features of the patient's head. For example, a camera (e.g., still, video, infrared, etc.) and/or computer vision sensors/tags can be used to monitor patient and/or clinical device movement to develop a pattern of patient interaction with the clinical device over a period of time.

At block 960, a deviation from the clinical protocol is identified based on the monitored pattern of patient interaction with the clinical device, a biometric indicator from the patient, and a desired setpoint state in the clinical protocol. For example, a difference in spirometry usage frequency, duration, position, etc., by the patient that is identified in the monitored pattern of patient interaction with the spirometer when compared to the spirometry clinical protocol can be quantified as a deviation (e.g., a quantified difference or other deviation in spirometer usage frequency, duration, position/orientation, etc.).

At block 970, when a deviation is identified, feedback proportional to the deviation from the clinical protocol is provided. In certain examples, the feedback can include an adjustment with respect to the series of prescribed tasks in the clinical protocol and/or an adjustment of at least one of orientation and position of the clinical device with respect to the patient's head. In certain examples, feedback can also include an indication of a degree of the patient's response to an incentive intervention and/or an ability of a care provider to directly provide care for an immobile or impaired patient.

At block 980, at least one of the combination of alarms and incentives is triggered with respect to the patient based on deviation and feedback. Which alarm(s) and/or incentive(s) is/are triggered differs based on a) whether a deviation has been identified at block 960, an extent/magnitude of that deviation, and the feedback provided at block 970. For example, if a deviation of patient behavior from the clinical protocol is slight, a positive incentive and reminder can be provided. However, if the deviation is large (e.g., greater than a threshold), then an incentive can be provided along with alarms alerting the patient as well as a care provider and/or other support personnel regarding dangers of not complying with the care protocol.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Figure 10:
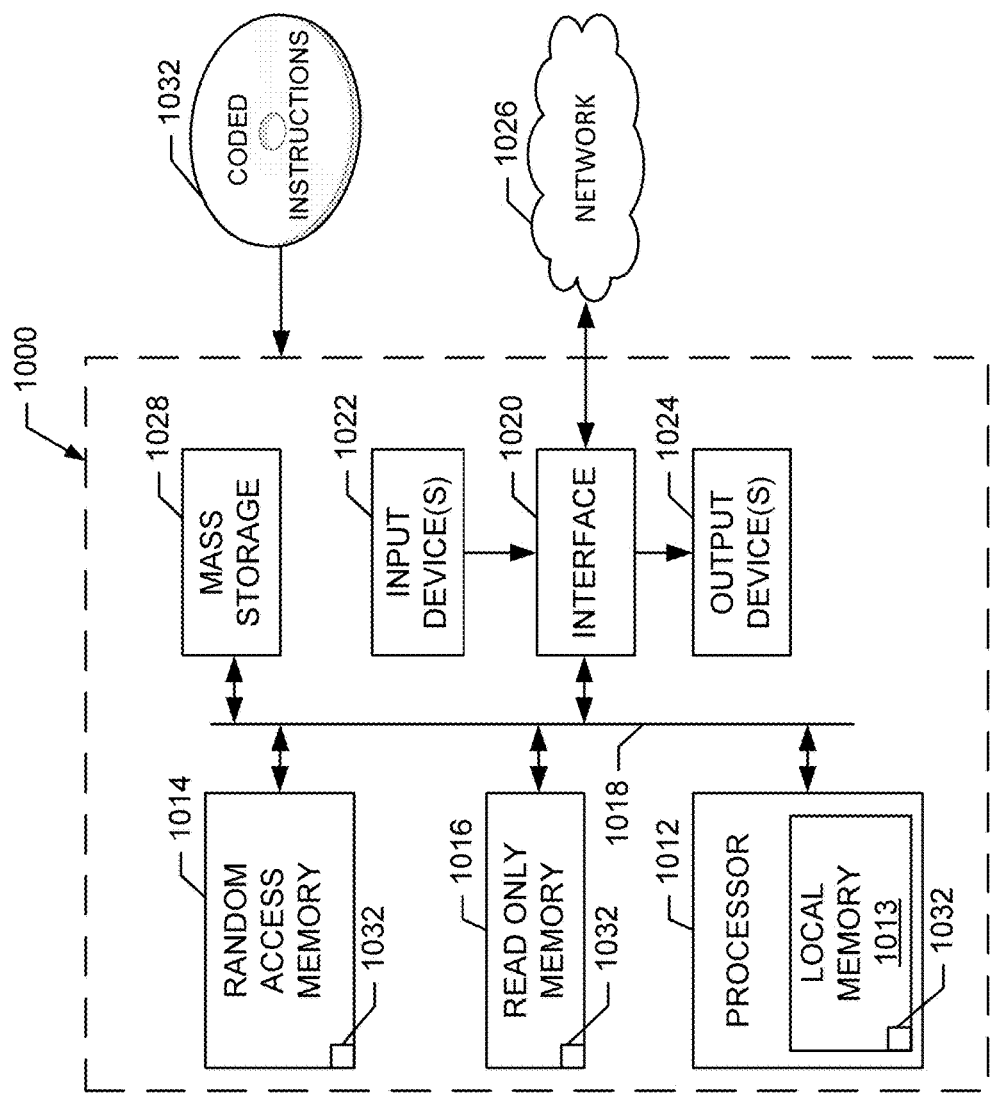
FIG. 10 is a block diagram of an example processor platform 1000 capable of executing instructions to implement the example systems and methods of FIGS. 1-9.

FIG. 10 is a block diagram of an example processor platform 1000 capable of executing instructions to implement the example systems and methods of FIGS. 1-9. The processor platform 1000 can be, for example, a server, a personal computer, a mobile device (e.g., a cell phone, a smart phone, a tablet such as an IPAD™) a personal digital assistant (PDA), an Internet appliance, or any other type of computing device.

The processor platform 1000 of the illustrated example includes a processor 1012. Processor 1012 of the illustrated example is hardware. For example, processor 1012 can be implemented by one or more integrated circuits, logic circuits, microprocessors or controllers from any desired family or manufacturer.

Processor 1012 of the illustrated example includes a local memory 1013 (e.g., a cache). Processor 1012 of the illustrated example is in communication with a main memory including a volatile memory 1014 and a non-volatile memory 1016 via a bus 1018. Volatile memory 1014 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 can be implemented by flash memory and/or any other desired type of memory device. Access to main memory 1014, 1016 is controlled by a memory controller.

Processor platform 1000 of the illustrated example also includes an interface circuit 1020. Interface circuit 1020 can be implemented by any type of interface standard, such as an Ethernet interface, a universal serial bus (USB), and/or a PCI express interface.

In the illustrated example, one or more input devices 1022 are connected to the interface circuit 1020. Input device(s) 1022 permit(s) a user to enter data and commands into processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to interface circuit 1020 of the illustrated example. Output devices 1024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 1020 of the illustrated example, thus, typically includes a graphics driver card, a graphics driver chip or a graphics driver processor.

Interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

Processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

Coded instructions 1032 associated with any of FIGS. 1-20 can be stored in mass storage device 1028, in volatile memory 1014, in the non-volatile memory 1016, and/or on a removable tangible computer readable storage medium such as a CD or DVD.

It may be noted that operations performed by the processor platform 1000 (e.g., operations corresponding to process flows or methods discussed herein, or aspects thereof) may be sufficiently complex that the operations may not be performed by a human being within a reasonable time period.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
    determining, using a configured processor, a ventilator protocol for a patient, the ventilator protocol including a series of prescribed tasks using a ventilator mask with respect to the patient to address a clinical condition;
    classifying, using the configured processor, the patient's lung function risk based on a comparison of a) patient attributes including at least one of lung capacity or lung impairment and b) tasks specified to be executed in the ventilator protocol;
    generating, using the configured processor, a combination of alarms and incentives for compliance with the ventilator protocol customized in at least one of frequency pattern, intensity, or position for the patient based on the patient attributes, the tasks to be executed in the ventilator protocol, and the patient's lung function risk;
    determining, using the configured processor, an orientation and position of the ventilator mask with respect to the patient's head based on an identified shape of the ventilator mask classified from sensor and camera data compared to an identified shape of the patient's head classified from the sensor and camera data, the position of the ventilator mask determined based on a distance between the patient's head and the ventilator mask measured using the identified shapes of the patient's head and the ventilator mask classified from the sensor and camera data, and the orientation of the ventilator mask determined with respect to an orientation of the patient's head, the orientation of the patient's head determined using shape classification of features of the patient's head and the orientation of the ventilator mask determined with respect to the orientation of the patient's head in a plurality of planes;
    monitoring, using the configured processor, a pattern of patient interaction with the ventilator mask over time based on the determined orientation and position of the ventilator mask with respect to the patient's head tracked over a period of time using the identified shape of the ventilator mask compared to the identified shape of the patient's head;
    identifying, using the configured processor, a deviation from the ventilator protocol based on the monitored pattern of patient interaction with the ventilator mask, a biometric indicator from the patient, and a desired setpoint state in the ventilator protocol, the desired setpoint state based on the at least one of frequency pattern, intensity, or position customized for the patient;
    when a deviation is identified, providing, using the configured processor, feedback proportional to the deviation from the ventilator protocol, the feedback including at least one of a) an adjustment with respect to the series of prescribed tasks in the ventilator protocol and b) an adjustment of at least one of orientation and position of the ventilator mask with respect to the patient's head; and
    triggering, using the configured processor, at least one of the combination of alarms and incentives with respect to the patient based on deviation and feedback, wherein the at least one of the combination of alarms and incentives differs based on a) whether a deviation is identified, b) an extent of the deviation, and c) the feedback provided.

2. The method of claim 1, wherein the ventilator protocol comprises a ventilator-acquired pneumonia protocol, and wherein the ventilator mask is associated with tubing.

3. The method of claim 1, wherein the ventilator protocol further uses a non-ventilator device in at least a portion of the series of prescribed tasks.

4. The method of claim 1, wherein the combination of alarms and incentives is further generated based on matched attributes of other patients and stakeholders to engage in providing interaction and assistance for the patient with respect to the ventilator protocol.

5. The method of claim 1, wherein the combination of alarms and incentives includes activation of social structures with an affinity or shared interest to provide ventilator protocol adherence and goal achievement incentive.

6. The method of claim 1, wherein feedback further includes a degree of the patient's response to an incentive intervention with respect to the ventilator protocol that is at least one of delivered to the patient as feedback and used to activate social structures with an affinity or shared interest with the patient to provide ventilator protocol adherence and goal achievement incentive.

7. The method of claim 1, wherein determining the orientation and position of the ventilator mask with respect to the patient's head further includes detecting a location of the ventilator mask using an active optical tag emitting at least one of visible and infrared light in a structured emission pattern that is sensed by an optical input in at least one of still and streaming video from the camera to orient the position of the ventilator mask in addition to an x-y-z coordinate location of the ventilator mask.

8. The method of claim 1, wherein identifying a deviation further includes detecting, using the configured processor as a reasoning engine, an anomaly in the monitored pattern of patient interaction.

9. The method of claim 8, wherein identifying a deviation further includes calculating, using the configured processor, a state of monitored people and objects to identify deviation from a desired state.

10. A tangible computer-readable storage medium including instructions which, when executed, particularly configure a processor to implement a method, the method comprising:

determining, using a configured processor, a ventilator protocol for a patient, the ventilator protocol including a series of prescribed tasks using a ventilator mask with respect to the patient to address a clinical condition;

classifying, using the configured processor, the patient's lung function risk based on a comparison of a) patient attributes including at least one of lung capacity or lung impairment and b) tasks specified to be executed in the ventilator protocol;

generating, using the configured processor, a combination of alarms and incentives for compliance with the ventilator protocol customized in at least one of frequency pattern, intensity, or position for the patient based on the patient attributes, the tasks to be executed in the ventilator protocol, and the patient's lung function risk;

determining, using the configured processor, an orientation and position of the ventilator mask with respect to the patient's head based on an identified shape of the ventilator mask classified from sensor and camera data compared to an identified shape of the patient's head classified from the sensor and camera data, the position of the ventilator mask determined based on a distance between the patient's head and the ventilator mask measured using the identified shapes of the patient's head and the ventilator mask classified from the sensor and camera data, and the orientation of the ventilator mask determined with respect to an orientation of the patient's head, the orientation of the patient's head determined using shape classification of features of the patient's head and the orientation of the ventilator mask determined with respect to the orientation of the patient's head in a plurality of planes;

monitoring, using the configured processor, a pattern of patient interaction with the ventilator mask over time based on the determined orientation and position of the ventilator mask with respect to the patient's head tracked over a period of time using the identified shape of the ventilator mask compared to the identified shape of the patient's head;

identifying, using the configured processor, a deviation from the ventilator protocol based on the monitored pattern of patient interaction with the ventilator mask, a biometric indicator from the patient, and a desired setpoint state in the ventilator protocol, the desired setpoint state based on the at least one of frequency pattern, intensity, or position customized for the patient;

when a deviation is identified, providing, using the configured processor, feedback proportional to the deviation from the ventilator protocol, the feedback including at least one of a) an adjustment with respect to the series of prescribed tasks in the ventilator protocol and b) an adjustment of at least one of orientation and position of the ventilator mask with respect to the patient's head; and triggering, using the configured processor, at least one of the combination of alarms and incentives with respect to the patient based on deviation and feedback, wherein the at least one of the combination of alarms and incentives differs based on a) whether a deviation is identified, b) an extent of the deviation, and c) the feedback provided.

11. The computer-readable storage medium of claim 10, wherein the ventilator protocol comprises a ventilator-acquired pneumonia protocol, and wherein the ventilator mask is associated with tubing.

12. The computer-readable storage medium of claim 10, wherein the ventilator protocol further uses a non-ventilator device in at least a portion of the series of prescribed tasks.

13. The computer-readable storage medium of claim 10, wherein the combination of alarms and incentives is further generated based on matched attributes of other patients and stakeholders to engage in providing interaction and assistance for the patient with respect to the ventilator protocol.

14. The computer-readable storage medium of claim 10, wherein the combination of alarms and incentives includes activation of social structures with an affinity or shared interest to provide ventilator protocol adherence and goal achievement incentive.

15. The computer-readable storage medium of claim 10, wherein feedback further includes a degree of the patient's response to an incentive intervention with respect to the ventilator protocol that is at least one of delivered to the patient as feedback and used to activate social structures with an affinity or shared interest with the patient to provide ventilator protocol adherence and goal achievement incentive.

16. The computer-readable storage medium of claim 10, wherein determining the orientation and position of the ventilator mask with respect to the patient's head further includes detecting a location of the ventilator mask using an active optical tag emitting at least one of visible and infrared light in a structured emission pattern that is sensed by an optical input in at least one of still and streaming video from the camera to orient the position of the ventilator mask in addition to an x-y-z coordinate location of the ventilator mask.

17. The computer-readable storage medium of claim 10, wherein identifying a deviation further includes detecting, using the configured processor as a reasoning engine, an anomaly in the monitored pattern of patient interaction.

18. The computer-readable storage medium of claim 17, wherein identifying a deviation further includes calculating, using the configured processor, a state of monitored people and objects to identify deviation from a desired state.

* * * * *